US012609206B2

(12) United States Patent
Dutta-Moscato et al.

(10) Patent No.: US 12,609,206 B2
(45) Date of Patent: *Apr. 21, 2026

(54) METHODS FOR MODELING HEPATIC INFLAMMATION

(71) Applicant: University of Pittsburgh—Of the Commonwealth System of Higher Education, Pittsburgh, PA (US)

(72) Inventors: Joyeeta Dutta-Moscato, Pittsburgh, PA (US); Yoram Vodovotz, Sewickley, PA (US); Liang-I Kang, Clayton, MO (US); Kari Nejak-Bowen, Wexford, PA (US); Qi Mi, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1394 days.

This patent is subject to a terminal disclaimer.

(21) Appl. No.: 17/243,066

(22) Filed: Apr. 28, 2021

(65) Prior Publication Data

US 2021/0375477 A1 Dec. 2, 2021

Related U.S. Application Data

(63) Continuation of application No. 15/223,367, filed on Jul. 29, 2016, now Pat. No. 11,004,543, which is a continuation of application No. 13/700,244, filed as application No. PCT/US2011/039400 on Jun. 7, 2011, now abandoned.

(60) Provisional application No. 61/352,116, filed on Jun. 7, 2010.

(51) Int. Cl.
*G16H 50/50* (2018.01)
*G16B 50/00* (2019.01)

(52) U.S. Cl.
CPC ............. *G16H 50/50* (2018.01); *G16B 50/00* (2019.02)

(58) Field of Classification Search
None
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,270,192 A | 12/1993 | Li et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,605,835 A | 2/1997 | Hu et al. |
| 5,645,860 A | 7/1997 | Knapp, Jr. et al. |
| 5,753,267 A | 5/1998 | Badylak et al. |
| 5,762,966 A | 6/1998 | Knapp, Jr. et al. |
| 5,771,969 A | 6/1998 | Garay |
| 5,866,414 A | 2/1999 | Badylak et al. |
| 6,099,567 A | 8/2000 | Badylak et al. |
| 6,472,200 B1 | 10/2002 | Mitrani |
| 6,485,723 B1 | 11/2002 | Badylak et al. |
| 6,509,147 B1 | 1/2003 | Altrichter et al. |
| 6,576,265 B1 | 6/2003 | Spievack |
| 6,579,538 B1 | 6/2003 | Spievack |
| 6,582,955 B2 | 6/2003 | Martinez et al. |
| 6,696,270 B2 | 2/2004 | Badylak et al. |
| 6,759,245 B1 | 7/2004 | Toner et al. |
| 6,783,776 B2 | 8/2004 | Spievack |
| 6,793,939 B2 | 9/2004 | Badylak et al. |
| 6,849,273 B2 | 2/2005 | Spievack |
| 6,852,339 B2 | 2/2005 | Spievack |
| 6,858,146 B1 | 2/2005 | Myers et al. |
| 6,861,074 B2 | 3/2005 | Spievack |
| 6,887,495 B2 | 5/2005 | Spievack |
| 6,890,562 B2 | 5/2005 | Spievack |
| 6,890,563 B2 | 5/2005 | Spievack |
| 6,890,564 B2 | 5/2005 | Spievack |
| 6,893,666 B2 | 5/2005 | Spievack |
| 7,160,719 B2 | 1/2007 | Nyberg |
| 7,273,465 B2 | 9/2007 | Ash |
| 2003/0017142 A1 | 1/2003 | Toner et al. |
| 2003/0087285 A1 | 5/2003 | Chow et al. |
| 2004/0067507 A1 | 4/2004 | Nolan et al. |
| 2005/0003535 A1 | 1/2005 | Gerlach |
| 2005/0015064 A1 | 1/2005 | Gerlach |
| 2005/0032218 A1 | 2/2005 | Gerlach |
| 2005/0049581 A1 | 3/2005 | Gerlach |

(Continued)

FOREIGN PATENT DOCUMENTS

| | | |
|---|---|---|
| WO | 2008067042 A2 | 6/2008 |
| WO | 2008150720 A1 | 12/2008 |
| WO | 2009042768 A1 | 4/2009 |

OTHER PUBLICATIONS

Plushner, Tocilizumab: An Interleukin-6 Receptor Inhibitor for the Treatment of Rheumatoid Arthritis, The Annals of Pharmacotherapy, Nov. 2008, pp. 1660-1668, vol. 42.

(Continued)

*Primary Examiner* — Lori A. Clow
(74) *Attorney, Agent, or Firm* — The Webb Law Firm

(57) ABSTRACT

Provided herein are in silico methods of modeling hepatic inflammation, fibrosis/cirrhosis, and cancer. The models are computer-implemented agent-based models and are useful in determining patient prognoses in hepatic conditions, including viral infections, damage, inflammation, and cancer. The modeling system also is useful in modeling the effects of active agents on normal hepatic tissue or hepatic tissue perturbed by inflammation, infection, damage, fibrosis/cirrhosis, and cancer.

20 Claims, 5 Drawing Sheets

(56)     References Cited

U.S. PATENT DOCUMENTS

| | | |
|---|---|---|
| 2005/0182349 A1 | 8/2005 | Linde et al. |
| 2007/0249538 A1 | 10/2007 | Sazani et al. |
| 2008/0145442 A1 | 6/2008 | Yarmush et al. |
| 2008/0228456 A1 | 9/2008 | Clermont et al. |
| 2008/0279766 A1 | 11/2008 | Everson et al. |

OTHER PUBLICATIONS

Prince et al., In Silico and In Vivo Approach to Elucidate the Inflammatory Complexity of CD14-deficient Mice, Mol. Med, Apr.-Jun. 2006, pp. 88-96, vol. 12, Nos. 4-6.
Ramadori et al., Inflammation, Damage Repair, Immune Cells, and Liver Fibrosis: Specific or Nonspecific, This Is The Question, Gastroenterology, 2004, pp. 997-1000, vol. 127, No. 3.
Redd et al., Wound Healing and Inflammation: Embryos Reveal the Way to Perfect Repair, Phil. Trans. R. Soc. Lond B, 2004, pp. 777-784, vol. 359.
Reynolds et al., A Reduced Mathematical Model of the Acute Inflammatory Response: I. Derivation of Model and Analysis of Anti-Inflammation, Journal of Theoretical Biology, 2006, pp. 220-236, vol. 242, No. 1.
Sheikh-Bahaei et al., Agent-Based Simulation of In Vitro Hepatic Drug Metabolism: In Silico Hepatic Intrinsic Clearance, 2005 Spring Simulation Multiconference. 6 pages.
Sheikh-Bahaei et al., Prediction of In Vitro Hepatic Biliary Excretion Using Stochastic Agent-Based Modeling and Fuzzy Clustering, Proceedings of the 2006 Winter Simulation Conference, pp. 1617-1624.
Starling, On the Absorption of Fluids from the Connective Tissue Spaces, Journal of Physiol., 1896, pp. 312-326, vol. 19, No. 4.
Szymczak et al., Correction of Multi-Gene Deficiency in vivo Using a Single 'Self-Cleaving' 2A Peptide-based Retroviral Vector, Nature Biotechnology, May 2004, pp. 589-594, vol. 22, No. 5.
Torres et al., Mathematical Modeling of Posthemorrhage Inflammation in Mice: Studies using a Novel, Computer-Controlled, Closed-Loop Hemorrhage Apparatus, Shock, 2009, pp. 172-178, vol. 32 No. 2.
Upperman et al., Mathematical Modeling in Necrotizing Enterocolitis—a New Look at an Ongoing Problem, Journal of Pediatric Surgery, 2007, pp. 445-453, vol. 42.
Vodovotz, Deciphering the Complexity of Acute Inflammation Using Mathematical Models, Immunologic Research, 2006, pp. 237-245, vol. 36, Nos. 1-3.
Vodovotz et al., Mathematical Models of the Acute Inflammatory Response, Current Opinion in Critical Care, 2004, pp. 383-390, vol. 10.
Vodovotz et al., Mechanistic Simulations of Inflammation: Current State and Future Prospects, Mathematical Biosciences, 2009, pp. 1-10, vol. 217.
Vodovotz et al., Translational Systems Biology of Inflammation, PLoS Computational Biology, Apr. 2008, pp. 1-6, vol. 4, issue 4.
Wang et al., Mathematical Analysis and Quantification of Fluorescent Proteins as Transcriptional Reporters, Biophysical Journal, Mar. 2008, pp. 2017-2026, vol. 94.
Waniewski et al., A Mathematical Model of Extracorporeal Antibody Removal in Autoimmune Disease, The International Journal of Artifical Organs, 1989, pp. 471-476, vol. 12, No. 7.
Yuan et al., Pathophysiology of Tumor-Associated Macrophages, Advances in Clinical Chemistry, 2008, pp. 199-223, vol. 45.
Zamora et al., Transforming Growth Factor-beta in Critical Illness, Crit Care Med, 2005, pp. s478-s481, vol. 33, No. 12.
Zeilinger et al., Time Course of Primary Liver Cell Reorganization in Three-Dimensional High-Density Bioreactors for Extracorporeal Liver Support: An Immunohistochemical and Ultrastructural Study, Tissue Engineering, 2004, pp. 1113-1124, vol. 10, No. 7/8.
An et al., From Artificial Life to In Silico Medicine: NetLogo as a Means of Translational Knowledge Representation in Biomedical Research, 2009, pp. 183-214.

Aggarwall et al., TNF Blockade: An Inflammatory Issue, Ernst. Schering. Research Foundation Workshop, 2006, pp. 161-186, vol. 56.
Aller et al., Posttraumatic Inflammation is a Complex Response Based on the Pathological Expression of the Nervous, Immune, and Endocrine Functional Systems, Society for Experimental Biology and Medicine, 2004, pp. 170-181, vol. 229.
An, Agent-Based Computer Simulation and SIRS: Building a Bridge Between Basic Science and Clinical Trials, Shock, 2001, pp. 266-273, vol. 16, No. 4.
An et al., Agent-Based Models in Translational Systems Biology, Wiley Interdiscip Rev. Syst. Biol. Med., 2009, pp. 159-171, vol. 1, No. 2.
An et al., Challenges and Rewards on the Road to Translational Systems Biology in Acute Illness: Four Case Reports from Interdisciplinary Teams, J. Crit Care, Jun. 2007, pp. 169-175, vol. 22, No. 2.
An, Introduction of an Agent-Based Multi-Scale Modular Architecture for Dynamic Knowledge Representation of Acute Inflammation, Theoretical Biology and Medical Modelling, May 2008, vol. 5, No. 11. 20 pages.
An et al., Translational Systems Biology: Introduction of an Engineering Approach to the Pathophysiology of the Burn Patient, J. Burn Care Res, 2008, pp. 277-285, vol. 29, No. 2.
Ancey et al., A Fusion Protein of the gp130 and Interleukin-6Ralpha Ligand-binding Domains Acts as a Potent Interleukin-6 Inhibitor, The Journal of Biological Chemistry, 2003, pp. 16968-16972, vol. 278, No. 19.
Annes et al., Making Sense of Latent TGFbeta Activation, Journal of Cell Science, 2003, pp. 217-224, vol. 116.
Bottinger et al., The Recombinant Proregion of Transforming Growth Factor beta1 (Latency-associated Peptide) Inhibits Active Transforming Growth Factor beta1 in Transgenic Mice, Proc. Natl. Acad. Sci., Jun. 1996, pp. 5877-5882, vol. 93.
Brown et al., Complexities of Targeting Innate Immunity to Treat Infection, Trends in Immunology, 2007, pp. 260-266, vol. 28, No. 6.
Bruining, A General Description of Flows and Pressures in Hollow Fiber Membrane Modules, Chemical Engineering Science, 1989, pp. 1441-1447, vol. 44, No. 6.
Chow et al., The Acute Inflammatory Response in Diverse Shock States, Shock, 2005, pp. 74-84, vol. 24, No. 1.
Clermont et al., In Silico Design of Clinical Trials: A Method Coming of Age, Crit Care Med, 2004, pp. 2061-2070, vol. 32, No. 10.
Constantine et al., A Linear Code Parameter Search Algorithm with Applications to Immunology, Comput Optim Appl, 2009, pp. 155-171, vol. 42.
Constantine et al., A Parameter Search Algorithm Based on Optimal Linear Codes, International Journal of Pure and Applied Mathematics, 2006, pp. 9-22, vol. 31, No. 1.
Daun et al., An Ensemble of Models of the Acute Inflammatory Response to Bacterial Lipopolysaccharide in Rats: Results from Parameter Space Reduction, Journal of Theoretical Biology, 2008, pp. 843-853, vol. 253.
Day et al., A Reduced Mathematical Model of the Acute Inflammatory Response: II. Capturing Scenarios of Repeated Endotoxin Administration, J. Theor. Biol. pp. 235-256, 2006, vol. 242, No. 1.
Dennler et al., Direct Binding of Smad3 and Smad4 to critical TGF Beta-Inducible Elements in the Promoter of Human Plasminogen Activator Inhibitor-Type 1 Gene, The EMBO Journal, 1998, pp. 3091-3100, vol. 17, No. 11.
Dinarello, Therapeutic Strategies to Reduce IL-1 Activity in Treating Local and Systemic Inflammation, Current Opinion in Pharmacology, 2004, pp. 378-385, vol. 4.
Economides et al., Cytokine Traps: Multi-Component, High-affinity Blockers of Cytokine Action, Nature Medicine, Jan. 2003, pp. 47-52, vol. 9, No. 1.
Enosawa et al., Long-Term Culture of Glutamine Synthetase-Transfected HepG2 Cells in Circulatory Flow Bioreactor for Development of a Bioartificial Liver, Cell Transplantation, 2000, pp. 711-715, vol. 9.

(56)          References Cited

OTHER PUBLICATIONS

Ermentrout et al., Cellular Automata Approaches to Biological Modeling, J. Theor. Biol., 1993, pp. 97-133, vol. 160.

Federspiel et al., Gas Flow Dynamics in Hollow-Fiber Membranes, AIChE Journal, Jul. 1996, pp. 2094-2099, vol. 42, No. 7.

Fernandez-Botran et al., Soluble Cytokine Receptors in Biological Therapy, Expert Opin. Biol. Ther., 2002, pp. 585-605, vol. 2, No. 6.

Fidler, Macrophages and Metastasis—A Biological Approach to Cancer Therapy: Presidential Address, Cancer Research, Oct. 1985, pp. 4714-4726, vol. 45.

Fortenberry et al., Extracorporeal Therapies in the Treatment of Sepsis: Experience and Promise, Seminars in Pediatric Infectious Diseases, 2006, pp. 72-79, vol. 17.

Gallucci et al., Danger Signals: SOS to the Immune System, Current Opinion in Immunology, 2001, pp. 114-119, vol. 13.

Gerlach, Bioreactors for Extracorporeal Liver Support, Cell Transplantation, 2006, pp. S91-S103, vol. 15, supplement 1.

Gerlach et al., Comparison of Hollow Fibre Membranes for Hepatocyte Immobilisation in Bioreactors, International Journal of Artifical Organs, 1996, pp. 610-616, vol. 19, No. 10.

Gerlach et al., Endothelial Cell Seeding on Different Polyurethanes, Artifical Organs, 1989, pp. 144-147, vol. 13, No. 2.

Gerlach et al., Gas Supply Across Membranes in Bioreactors for Hepatocyte Culture, Artificial Organs, 1990, pp. 328-333, vol. 14, No. 5.

Goldring, Inflammatory Mediators as Essential Elements in Bone Remodeling, Calcif Tissue Int, 2003, pp. 97-100, vol. 73.

Goris, Pathophysiology of Shock in Trauma, European Journal of Surgery, 2000, pp. 100-111, vol. 166.

Guilak et al., The Role of Biomechanics and Inflammation in Cartilage Injury and Repair, Clinical Orthopaedics and Related Research, 2004, pp. 17-26, No. 423.

Hart, Inflammation. 1: Its Role in the Healing of Acute Wounds, Journal of Wound Care, 2002, pp. 205-209, vol. 11, No. 6.

Hart, Inflammation. 2: Its Role in the Healing of Chronic Wounds, Journal of Wound Care, 2002, pp. 245-249, vol. 11, No. 7.

Hasegawa et al., Modifying TNFalpha for Therapeutic Use: A Perspective on the TNF Receptor System, Mini Reviews in Medicinal Chemisty, 2001, pp. 5-16, vol. 1.

Hipp et al., Spatially Invariant Vector Quantization: A Pattern Matching Algorithm for Multiple Classes of Image Subject Matter Including Pathology, J Pathol Inform, 2011, vol. 2, No. 13. 8 pages.

Hoofnagle, Acute Hepatitis C, Biomedical Research Reports, 2000, pp. 71-83, Academic Press.

Hoofnagle, Hepatitis C: The Clinical Spectrum of Disease, Hepatology, 1997, pp. 15s-20s.

Ilmuro et al., Antibodies to Tumor Necrosis Factor Alfa Attenuate Hepatic Necrosis and Inflammation Caused by Chronic Exposure to Ethanol in the Rat, Hepatology, 1997, pp. 1530-1537, vol. 26, No. 6.

Kelsey et al., Theoretical Analysis of Convective Flow Profiles in a Hollow-Fiber Membrane Bioreactor, Chemical Engineering Science, 1990, pp. 3211-3220, vol. 45, No. 11.

Kumar et al., A Mathematical Simulation of the Inflammatory Response to Anthrax Infection, Shock, 2008, pp. 104-111, vol. 29, No. 1.

Kumar et al., The Dynamics of Acute Inflammation, Journal of Theoretical Biology, 2004, pp. 145-155, vol. 230.

Lagoa et al., The Role of Initial Trauma in the Host's Response to Injury and Hemorrhage: Insights from a Correlation of Mathematical Simulations and Hepatic Transcriptomic Analysis, Shock, 2006, pp. 592-600, vol. 26, No. 6.

Li et al., A Patient-Specific in silico Model of Inflammation and Healing Tested in Acute Vocal Fold Injury, PLoS ONE, Jul. 2008, vol. 3, issue 7. 11 pages.

Lotze et al., High-Mobility Group Box 1 Protein (HMGB1): Nuclear Weapon in the Immune Arsenal, Nature Reviews Immunology, Apr. 2005, pp. 331-342, vol. 5.

Mi et al., Agent-Based Model of Inflammation and Wound Healing: Insights into Diabetic Foot Ulcer Pathology and the Role of Transforming Growth Factor-beta1, Wound Repair and Regeneration, 2007, pp. 671-682, vol. 15.

Nathan, Points of Control in Inflammation, Nature, Dec. 2002, pp. 846-852, vol. 420.

Hepatocytes          ⊘   Stellate cell

⊘  Kupffer cell       ▩▩▩  Collagen deposit (fibrosis)       ▨  Tumor

METHODS FOR MODELING HEPATIC INFLAMMATION

CROSS REFERENCE TO RELATED APPLICATIONS

This application is a continuation of U.S. patent application Ser. No. 15/223,367, filed Jul. 29, 2016, which is a continuation of U.S. patent application Ser. No. 13/700,244, which is a national stage of International Patent Application No. PCT/US2011/039400, filed Jun. 7, 2011, which claims the benefit of U.S. Provisional Patent Application No. 61/352,116, filed Jun. 7, 2010, each of which is incorporated herein by reference in its entirety.

BACKGROUND

This invention relates to the development of computer models for simulating and creating simulated depictions of inflammation of hepatic tissue and of hepatocellular carcinoma (HCC).

Various approaches have been used to construct simulations of complex biologic processes. All these methods have distinct advantages and disadvantages. In vitro biological systems work well in many situations, but require physical facilities and often are not complex enough or accurate enough to effectively model in vivo systems. In silico (computer-simulated) systems are becoming more sophisticated and, as described below, are becoming increasingly able to model biological systems. Two modeling systems are commonly, but not exclusively, utilized to model biological systems: equation-based modeling (EBM), or more specifically ordinary differential equations (ODE), and agent-based modeling (ABM).

The ODE type of modeling is a type of equation-based modeling that consists of establishing a series of differential equations that describe the sequential change in the states of the components of the system over time. The differential equations are derived from known and hypothesized kinetics of the components of the biologic system. This approach has been used for many years to describe chemical systems, for example Michaelis-Menten kinetics. The variables of the equations generally represent average concentrations of the various components. These systems of equations are generally most accurate in settings in which large numbers of individuals of these components are assumed to exist and to exert their effects in aggregate. When the numbers become small, differential equation descriptions break down. The behavior of the system with limited spatial information (e.g. compartments) can be characterized with ODE; if more precise spatial resolution is desired, partial differential equations (PDE) are more commonly used. If simple enough, ODE can be solved analytically. If not, they can be easily solved computationally using a variety of commercially available and free software, as well as proprietary software designed for specific implementations of ODE models. Additionally, methods from nonlinear analysis can explore the properties of ODE without completely solving them. Because these equations are based on and describe biologic interactions, these models can potentially predict outcomes beyond the range of data on which these models were initially calibrated. In this latter aspect, EBM is different from statistical models. Furthermore, manipulation of a biologic mechanism can be entered into the model and an outcome derived (predicted).

The ABM type of modeling focuses on the rules and mechanisms of behavior of the individual components of a system, and may be more accurate than EBM in settings in which the stochastic actions of these agents is a better approximation of biological reality as compared to the actions of these components in aggregate. The components of a system are classified into types of "agents" by virtue of shared mechanisms that have been identified experimentally. The mechanisms are expressed as a series of conditional ("if-then") statements, and computer programs are written to describe the rules of behavior. An example would be the sequence of receptor activation involved in neutrophil adhesion. The model defines a "virtual world" based on characteristics of the reference system and generates populations of the various types of agents. The agents interact based on responses (defined by their rule systems) to inputs and outputs from their environment. For example, simulated cells would respond to variables in their immediate neighborhood, representing the extent of a cell's interaction with its extracellular milieu. The agents run in a parallel fashion to simulate simultaneous behavior, and the dynamics of the system are allowed to emerge from the multiple interactions among the agents over time. Consequently, all measured parameters and outcomes from the model are generated by the actions of the agents. The rules governing the behavior of agents should ideally be well-vetted, simple rules. Because ABMs are mechanistic models, any intervention that deals with a defined mechanism in the model can be simulated. Because they are based on rules, ABMs are often more intuitive to non-mathematicians than EBM (Ermentrout, G. B., et al. (1993). Journal of Theoretical Biology, 160(1), 97-133; An G. Agent-based computer simulation and SIRS: building a bridge between basic science and clinical trials. Shock 2001; 16(4):266-73; Vodovotz Y, Clermont G, Chow C, An G. Mathematical models of the acute inflammatory response. Curr Opin Crit Care 2004; 10:383-90; Vodovotz, Y., Csete, M.; Bartels, J.; Chang, S.; An, G. Translational systems biology of inflammation. PLoS Comput. Biol. 2008. 4:1-6; An, G.; Mi, Q.; Dutta-Moscato, J.; Solovyev, A.; Mikheev, M.; Vodovotz, Y. Agent-based models in translational systems biology. Wiley Interdisciplinary Reviews—Systems Biology. 2009. 1:159-171).

Inflammation and cancer are often interlinked. In the liver, hepatic inflammation can lead to fibrosis, cirrhosis, and cancer, e.g., hepatocellular carcinoma (HCC). For example, the failure of a patient's immune system to adequately clear an infection, such as in a chronic infection by Hepatitis C virus (HCV), results in liver inflammation and in some cases HCC. Development and calibration of a realistic model of liver inflammation, fibrosis, cirrhosis, and cancer development is hampered by the long-term nature of the related diseases and with respect to obtaining early-stage disease and multiple biopsies over time. Liver biopsies pose hazard to the patient, and are only taken when it is necessary. As such, early-stage biopsy data and multiple time point samples over the course of the disease are very rare.

SUMMARY

Provided herein are systems and methods of modeling hepatic inflammation, fibrosis and cancer. The systems and methods are useful for determining independent patient prognoses, as well as for drug development and testing and integrated digital pathology.

According to one embodiment, methods and systems of modeling progression of hepatic inflammation in a patient is provided. The method comprises inputting test data into an agent-based computer-implemented modeling system of hepatic inflammation, running the model, and producing output of the modeling system that comprises one or more of the following for one or more future time points: inflammation state, viral load, viral damage, presence of a tumor, size of a tumor, presence of cancer (metastasis), size or extent of metastasis, state of fibrosis and/or eventual cirrhosis. The agent-based computer-implemented modeling system comprises a plurality of agents and measurable factors, the agents, including biological elements of liver inflammation, fibrosis and cancer, such as hepatocytes, macrophages, stellate cells and tumor cells; and measurable factors, such as the inflammatory cytokine tumor necrosis factor-$\alpha$ (TNF-$\alpha$), the cytokine transforming growth factor-$\beta$1 (TGF-$\beta$1), and the damage-associated molecular pattern molecule ("danger signal") high-mobility group box-1 (HMGB1).

DETAILED DESCRIPTION

Figure 1:
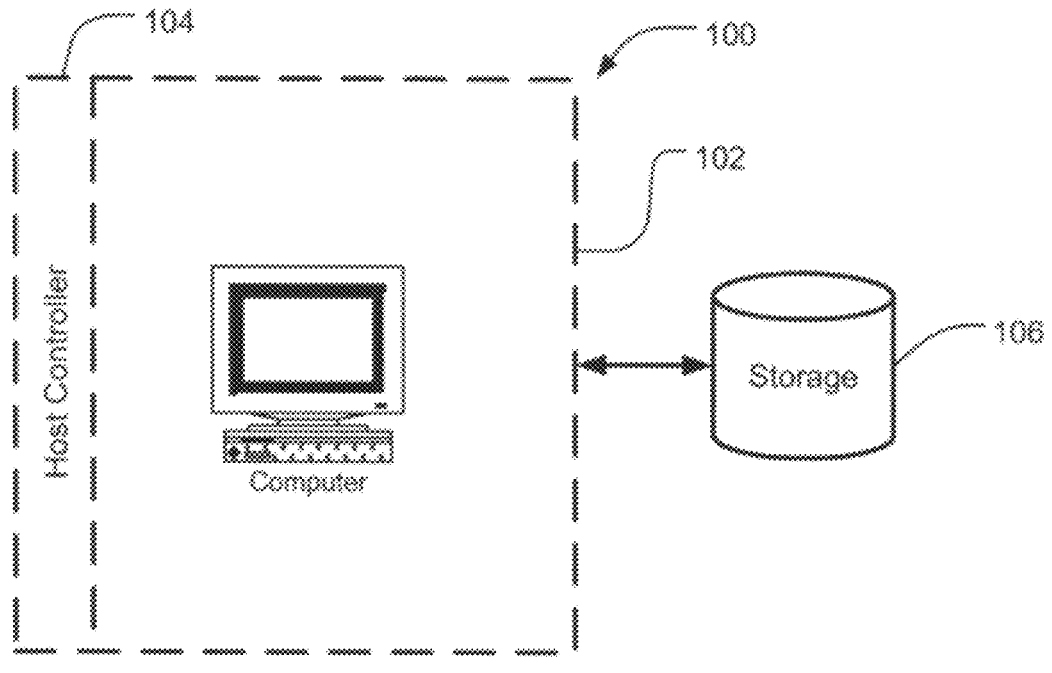
FIG. 1 illustrates one embodiment of a computer system for implementing a modeling system as described below.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases.

As used herein, the terms "comprising," "comprise" or "comprised," and variations thereof, are meant to be open ended. The terms "a" and "an" are intended to refer to one or more.

As used herein, the term "patient" or "subject" refers to members of the animal kingdom including but not limited to human beings and "mammal" refers to all mammals, including, but not limited to human beings.

As indicated above, a system and method are provided for modeling progression of the inter-related conditions of hepatic inflammation, fibrosis and cancer in a patient. The systems and methods are computer-implemented. The method comprises inputting test data into an agent-based computer-implemented modeling system of hepatic inflammation, running the model, and producing output of the modeling system that comprises one or more of the following for one or more future time points: hepatic tissue structure, hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof. The agent-based computer-implemented modeling system is implemented on at least one computer with a computer readable medium having programming instructions stored thereon. In the system, the programming instructions, when executed by a processor of the at least one computer, cause the processor to: receive or define at least one of the following: agent data, global data, initialization process data, or any combination thereof, the agent data comprising at least one of the following: definition data, behavior data, class data, internal state data, function data, link data, space data, or any combination thereof; model the at least one hepatic condition associated with at least one agent based at least in part upon at least a portion of the agent data corresponding to the at least one agent; and generate modeling output data representative of at least one of the following: hepatic tissue structure, hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof. The agent data, global data, initialization process data, or any combination thereof represent biological elements of liver structure, such as portal triads and/or hepatic lobules, biological elements of liver inflammation, fibrosis and cancer, such as hepatocytes, macrophages, stellate cells and/or tumor cells; and measurable factors, such as TNF-$\alpha$, TGF-$\beta$1, and/or HMGB1. The model includes relevant cells, cytokines, and processes, including the response to tissue damage, the process by which cell death leads to a hypoxic core, and the process by which a hypoxic region stimulates tumor angiogenesis. The system and methods facilitate identification and testing of active agents (e.g., drugs) that prevent inflammation, tissue damage, fibrosis or cancer based on their impact on the model. Likewise, the systems and methods facilitate generation of exemplary representative digital representations of cell and tissue structure at any stage of the modeling process, permitting characterization of images of a sample biopsy obtained from a patient, and determining a patient's prognosis by comparison of the patient's test image with a library of the exemplary images.

The inflammation, fibrosis and cancer modeling platform described herein is generally useful since it allows for simulating the responses of a slice of liver to diverse insults that, in turn, lead to inflammation, which in turn leads to tissue damage and/or dysfunction, which with some probability will in turn heal appropriately or become fibrotic or cirrhotic, and which, with some probability, can allow for the uncontrolled proliferation of cancer stem cells (or cancer progenitor cells, which are functionally equivalent in this ABM). These cancer stem cells/progenitor cells will lead to the formation of a tumor, which can develop a hypoxic core that will develop new blood vessels and hence lead to further tumor growth as well as metastasis. This general-purpose nature of the simulation will allow for developing general therapeutic strategies for inflammation, fibrosis, cirrhosis, and cancer in the liver, under conditions specific to individuals or groups (e.g. situations in which there is a high level of baseline inflammation due to alcoholism [a risk factor for cirrhosis and liver cancer]), high cholesterol/ obesity, overdose of acetaminophen, exposure to liver toxins, chronic infections, or other diseases that affect the liver).

Based on the above attributes of the simulation, this simulation may be used for drug development and testing. The current methodology for the design of therapies for HCV-induced HCC is rooted in basic science and preclinical studies related to cancer treatment. The basic science studies are generally carried out in cell culture, which cannot reproduce the complex environment of cancer in vivo or the interaction between cancerous cells and surrounding healthy tissues. Preclinical studies are generally carried out in rodents that are either subjected to artificially administered doses of cancerous agents or genetically modified to develop HCC. These studies suffer from the limitations that the damage is acute and not chronic, that it occurs not through HCV infection but through alternate pathways to HCC that are chemically, genetically, or radioactively induced instead of virally induced, and that the progression of cancer in these animals differs in some respect from the human scenario. The strategy to be used for rational design of anti-liver cancer drugs, targeting various aspects of the inflammatory cascade, the fibrosis/cirrhosis process, the carcinogenesis process, or the tumor angiogenesis process embodied in the computational simulation, is to minimize overall tissue damage/dysfunction. A computerized algorithm would search the parameter space of the computational model of inflammation/cancer, in order to determine what changes to the parameters characteristic of the inflamed, fibrotic, cirrhotic, or cancerous state (in which damage/dysfunction is high) will result in reducing this damage/dysfunction to levels characteristic of a healthy tissue (and, concomitantly, to restore the healthy appearance of tissue biopsies). The iterative strategy would include verification of the effects of the drug on the various parameters both in vitro and in vivo, with verification of the reduction of damage/dysfunction in vivo. A therapeutic agent obtained via this strategy would be any agent that is derived from a computational simulation describing the inter-related cascade of inflammation, fibrosis/cirrhosis, and liver cancer and that culminates in tissue damage/dysfunction, and that is subsequently vetted in screening assays carried out both in vitro and in vivo. The efficacy of this agent is then subsequently tested in a simulated clinical trial, in which a variable population is generated using variation in insult size/inoculum as well as variation in inflammatory products. Below is an example of such a therapeutic strategy:

An automated search of the parameter space of the computational model described above suggests that a drug candidate that will reduce liver damage/dysfunction sufficiently to increase survival in a rat model of liver cancer will have the following properties: in vitro reduction of the responsiveness of liver macrophages (Kupffer cells) to HMGB1 as well as a reduction in the capacity of macrophages to produce TNF-α, in vitro elevation of the capacity of liver stellate cells to produce active TGF-β1, in vivo reduction in tissue levels of TNF-α and HMGB1, and an overall reduction in liver fibrosis observed histologically. This strategy would allow for the simulation of the effects of the proposed agent in a randomized, placebo-controlled clinical trial prior to carrying out such a trial, in order to further verify the clinical efficacy of the proposed drug.

One use of the ABM leverages the fact that this type of simulation can often reproduce a visual pattern of cells and tissue architecture, which in turn can be compared to a photomicrograph. Moreover, since the ABM recapitulates a biological process, additional information such as distribution of given molecules (e.g. inflammatory cytokines) can be depicted. This pattern can be compared to that seen upon immunostaining of tissue sections for such molecules.

The pattern observed in the ABM simulation is derived from a simulated biological process, and thus calibrating the ABM for the pattern observed in actual photomicrographs or immunostained tissue sections can yield a quantitatively predictive (in both time and levels of cells/mediators) that essentially leads to a patient-specific, personalized simulation of the cancer process. In addition, this mechanistic foundation of the simulation means that simulated therapies can be run in silico on a patient-specific basis. Thus, this platform allows for a "smart diagnostic", which not only can lead to better prediction of the course of disease, but that can also be used to suggest specific therapeutic options.

As used herein "agent-based modeling" is a rules-based, stochastic modeling framework in which agents obey simple rules that, as a whole, generate complex system behavior.

As used herein, a "differential equation" is an equation in which the derivatives of a function appear as variables. In equation-based modeling (EBM), the model is a set of equations, and execution consists of evaluating them. An ordinary differential equation (or ODE) is a relation that contains functions of only one independent variable, and one or more of its derivatives with respect to that variable.

As used herein a "biological system" is a subset or microcosm of the physical structure and/or activities that are present in a living organism, such as a cell, plant, animal, vertebrate or invertebrate. A biological system may be, without limitation, an organ, a biochemical or biological process, a biochemical process present in an organ, tissue or organism, a pathogen and infected tissue, diseased tissue, etc. In the context of the present disclosure, biological systems include, for example and without limitation, cells, tissue, organs, cells and factors (chemical compounds, proteins such as cytokines, DNA, RNA, and other cellular and non-cellular elements) involved in any fashion with the process of hepatic inflammation, fibrosis and cancer in any context. As such, "hepatic inflammation, fibrosis and cancer" refers to the process of liver inflammation caused, e.g., by hepatic viral infection or injury, and the progression of the inflammatory state to fibrosis (including, for example, cirrhosis) and/or cancer. Elements thereof include organs, tissue, cells and factors that are physically present and/or active in the biological system. As used herein, hepatic inflammation, fibrosis and cancer refer to hepatic inflammation, fibrosis and cancer, no matter the cause of the inflammation.

As used herein a "modeling system" is a computational framework by which a biological system is modeled. A modeling system embodies various elements of a biological system. As used herein an "element," in the context of modeling a biological system, means any components of the model, as described above, including, without limitation, agent data, global data, initialization process data, data layers, representative grids and images, and input parameters. For example, elements of the SPARK platform, described below include, for example: agents, spaces, data layers, the observer, links, etc.

A modeling system may be "calibrated" by assigning, relating, comparing, or otherwise comporting elements of a modeled system with actual data values obtained directly or in any other manner from actual data values, for example and without limitation, by statistical computation methods or other mathematical methods. Calibration typically involves iterative adjustment of model parameters needed to achieve a situation in which the output of a mathematical model matches the experimentally determined time courses of the analytes (variables) in the model. The quality of the model and the calibration procedure are typically assessed by a process of "validation", in which predictions of the model are tested against data withheld from the calibration procedure.

Modeling systems are implemented on a computing device (computer) as processes. In the context of computing, a process is, broadly speaking any computer-implemented activity that generates an outcome, such as implementation of a mathematical or logical formula or operation, algorithm, etc. FIG. 1 illustrates one embodiment of a system 100 for implementing a modeling system. The system 100 may include a device 102 operating under the command of a controller 104. Device 102 may be referred to herein, without limitation, as a computer or computing device. The broken lines are intended to indicate that in some implementations, the controller 104, or portions thereof considered collectively, may instruct one or more elements of the device 102 to operate as described. Accordingly, the functions associated with the modeling methods (e.g., processes, software, programs) described herein may be implemented as software executing in the system 100 and controlling one or more elements thereof. An example of a device 102 in accordance with one embodiment of the present invention is a general-purpose computer capable of responding to and executing instructions in a defined manner. Other examples include a special-purpose computer including, for example, a personal computer (PC), a workstation, a server, a laptop computer, a web-enabled telephone, a web-enabled personal digital assistant (PDA), a microprocessor, an integrated circuit, an application-specific integrated circuit, a micro-processor, a microcontroller, a network server, a Java™ virtual machine, a logic array, a programmable logic array, a micro-computer, a mini-computer, or a large frame computer, or any other component, machine, tool, equipment, or some combination thereof capable of responding to and executing instructions.

In one non-limiting embodiment, system 100 is implemented as a PC. Furthermore, the system 100 may include a central processing engine including a baseline processor, memory, and communications capabilities. The system 100 also may include a communications system bus to enable multiple processors to communicate with each other. In addition, the system 100 may include storage 106 in the form of computer readable medium/media, such as a disk drive, optical drive, a tape drive, flash memory (e.g., a non-volatile computer storage chip), cartridge drive, and control elements for loading new software. In embodiments of the invention, one or more reference values may be stored in a memory associated with the device 102. Data, such as images produced by the methods and systems described herein may be organized on computer readable media in a database, which is an organized collection of data for one or more purposes, usually in digital form.

Embodiments of the controller 104 may include, for example, a program, code, a set of instructions, or some combination thereof, executable by the device 102 for independently or collectively instructing the device 102 to interact and operate as programmed, referred to herein as "programming instructions". One example of a controller 104 is a software application (for example, operating system, browser application, client application, server application, proxy application, on-line service provider application, and/or private network application) installed on the device 102 for directing execution of instructions. In one embodiment, the controller 104 may be a Windows™ based operating system. The controller 104 may be implemented by utilizing any suitable computer language (e.g., C\C++, UNIX SHELL SCRIPT, PERL, JAVA™ JAVASCRIPT, HTML/DHTML/XML, FLASH, WINDOWS NT, UNIX/LINUX, APACHE, RDBMS including ORACLE, INFORMIX, and MySQL) and/or object-oriented techniques.

In one embodiment, the controller 104 may be embodied permanently or temporarily in any type of machine, component, physical or virtual equipment, storage medium, or propagated signal capable of delivering instructions to the device 102. In particular, the controller 104 (e.g., software application, and/or computer program) may be stored on any suitable computer readable media (e.g., disk, device, or propagated signal), readable by the device 102, such that if the device 102 reads the storage medium, the functions described herein are performed. For example, in one embodiment, the controller 104 may be embodied in various computer-readable media for performing the functions associated with processes embodying the modeling methods.

Liver models described herein may be implemented in a number of programming platforms for implementing Agent-based modeling applications for creating Agent-Based Models (ABMs) by use of Agent-Based Model Modules (ABMMs), which are computer processes for running ABMs. In the examples below, a custom-built programming platform, the Simple Platform for Agent-based Representation of Knowledge (SPARK) was used. SPARK is a stand-alone application written in the Java™ programming language. It provides a user-friendly interface, and a simple programming language for developing agent-based models (ABMs). SPARK has the following features specialized for modeling biomedical systems: 1) continuous space that can simulate real physical space; 2) flexible agent size and shape that can represent the relative proportions of various cell types; 3) multiple spaces that can concurrently simulate and visualize multiple scales in biomedical models; 4) a convenient graphical user interface. Other Agent-based modeling software include: StarLogo®, NetLogo®, Swarm, Repast, MASON, and Ascape. Among these, NetLogo® is one of the most popular for biomedical modeling, particularly by non-formally-trained programmers, due to its user-friendly interface and the natural language-like syntax of its Logo-based programming language. SPARK, along with the SPARK-PL language was designed with Logo-like syntax, so that users could benefit from some capabilities currently not found in NetLogo® and similar software. These include the special features of SPARK cited earlier, as well as the ability to organize code into modules that can map to biological processes, as well as offering the potential for parallelization in distributed computer architectures. Non-limiting examples of ODE software programs include: XPPAUT (an ODE simulation program), Mathematica® and MATLAB®; an ODE simulation program. Elements of EBM or ODE modeling can be readily implemented within ABM software.

The elements of the ABM models described herein are termed "agent data, global data, initialization process data, or any combination thereof" as generic for the various elements of each model, irrespective of the software package used. For instance in the context of SPARK, agent data, global data, initialization process data, or any combination thereof refer to agents, spaces (e.g., grids), data layers, links, the observer, etc.

Figure 2:
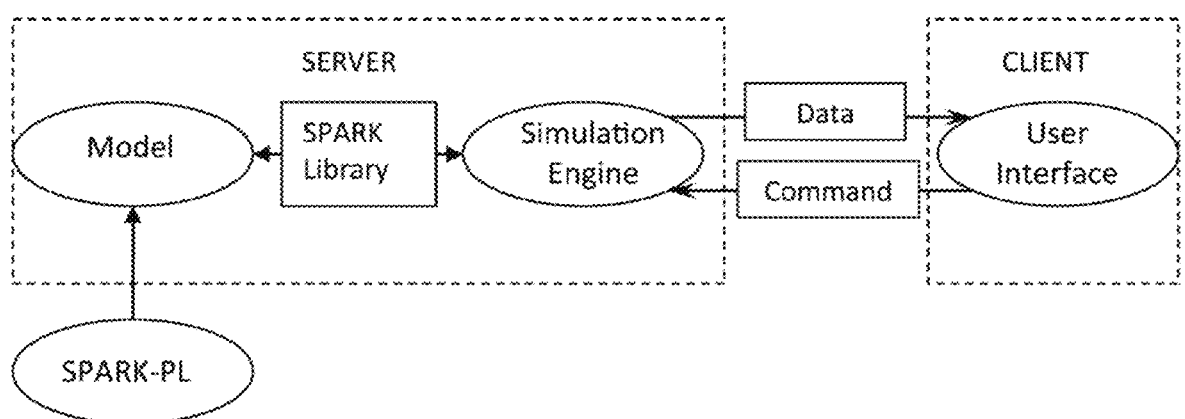
FIG. 2 is a flow diagram of the SPARK agent-based modeling software application as implemented in a client-server environment.

One embodiment of a useful Agent-Based Modeling software platform is SPARK, which is described in detail for illustrative purposes. SPARK is implemented as a client-server application. There are five main components which constitute SPARK (FIG. 2), including a specialized SPARK programming language (SPARK-PL) that can be used for model development. The use of SPARK-PL is optional; SPARK models can be written directly in Java™ as well. User models are created with the functionality provided by the SPARK library, which contains definitions of the main SPARK concepts: Agents, Spaces, Data Layers and the Observer. The simulation engine runs user models. It uses classes from the SPARK library to communicate with user models.

The user interface allows working with SPARK models interactively. Users can load models, set parameters of their choice, run simulations, and visualize results. The simulation engine is completely independent from the user interface. The user interface (which runs on a client machine) communicates with the simulation engine (which runs on the server) by sending commands to the server and by receiving data from the server. The received data can be saved on a disk, analyzed, or visualized by the client. In general, data sent by the server contains information about the state of a simulation: values of variables, positions of agents in a space, etc.

There are several possible implementations of the SPARK client and server. One option is to implement them inside the same program. In this case, the communication process will be very fast, but the client and server need to share the resources of the same machine. Another option is to implement the client and server as two separate programs, and establish the communication between them using a network interface.

In this situation, it is optimal not to send all data after each simulation step. Instead, data can be sent at specific time intervals using data buffers, or data can be collected and sent only after the end of a simulation. The two versions of the implementations of client and server are designed for different purposes of simulations. The first version can be applied for models with relatively short simulation time but requiring quick visualization of output. The latter version is suitable for large scale simulations where the users may want to view the results after thousands of simulation steps. In the standard SPARK distributions, both versions of the client and the server are available.

From a modeler's point of view, the most important components of SPARK are 1) the SPARK library; 2) SPARK-PL; and 3) the SPARK user interface. Key concepts of the SPARK library, the SPARK programming language, and the user interface are described below.

SPARK models are created by using basic components of the SPARK library. A SPARK model consists of the following elements: definitions of agents and a global model description. A model description includes the initialization process for a model (the "setup" method) and contains the global variables and parameters. It also includes methods which are called before and after each simulation step, and which are primarily used for changing global variables and collecting statistics.

Figure 3:
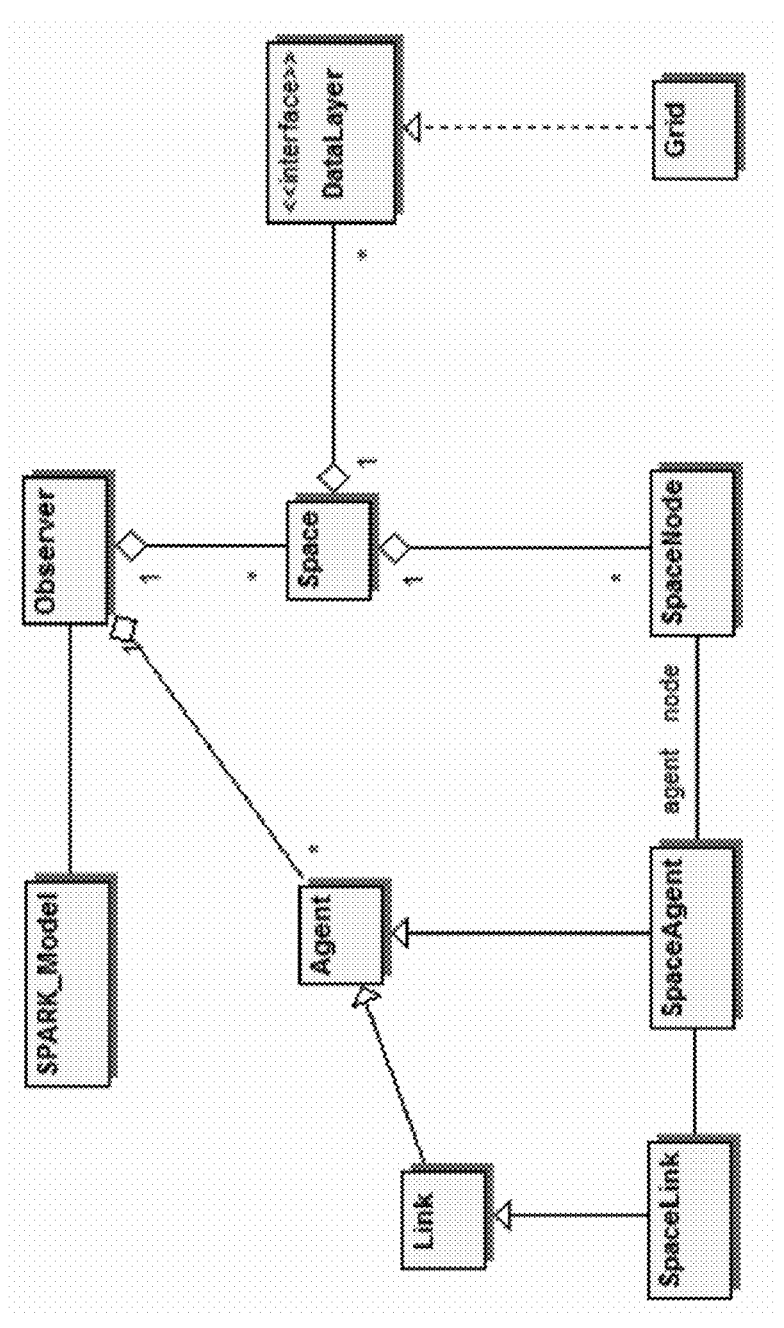
FIG. 3 is a diagram showing connection between main SPARK model components.

The main components of SPARK models are Space, Data Layers, Agents, Links, and the Observer (FIG. 3). Space is analogous to the physical space, and provides a context within which the model evolves. For example, the ABM contains spaces representing liver tissue as a contiguous layer of hepatocytes. Data Layers provide a means of tracking multiple variables within the same model. For example data layers can be used to track the amounts of the inflammatory cytokine tumor necrosis factor-$\alpha$ (TNF-$\alpha$). Agents can move, perform functions, interact with each other, and also interact with the space they occupy. Classes of agents can correspond to different cell types involved in inflammation, fibrosis and cancer. Each agent has its own set of behaviors and rules of action. For example, inflammatory cells (macrophages) are chemo-attracted and activated by platelets.

Links can be used to connect two or more agents together with various strengths and distances. Not all biomedical systems can be modeled using a number of independent agents. In some systems, agents are expected to link together. For instance, in normal situation, platelets in the blood can be represented as separate agents in a SPARK model; once these platelets are activated, however, they would change their shape and tightly bind together and also to the injured tissue. In this case, we need a way to build the connection among these agents. The Observer contains information about spaces and all agents in the model and also controls the simulation process.

A SPARK model consists of agents that have some predefined behavioral rules, and a global description of the model itself: classes of agents in the model, initialization process, global variables. Generally, the simulation proceeds as follows. First, the model is initialized. Then, the simulation loop begins. A global function, defined in a model class, is called at the beginning of each simulation step. Next, all agents are asked to perform their steps (execute their behavior function). After that, a global function for finalizing a step is called. The simulation ends when a predefined number of simulation steps is achieved, or when some user-defined conditions are met.

Agents are the central components of a SPARK model; the modeling process consists of creating agents and programming their behavior. Each agent can be characterized by two main features: its class (like inflammatory cell class) and its internal state. The internal state of an agent is the collection of variables and their values, which completely describe the agent. Agents of the same class have identical rules (the same functionality). In keeping with object oriented specifications, classes of agents form a hierarchical structure, with the base class called, simply, "Agent". The class is the first thing that is defined for any agent. Many operations in SPARK work directly with "Agent" classes.

For example, there are functions that return all agents of a specific class possessing some special properties (e.g., occupying some location in a space). One feature of an agent class is that all agents of the same class can be scheduled to act at specific time points (see the description of the Observer for more details). The behavior of each agent is specified in the "step" function defined for any agent. This function is the same for all agents of the same class. The only parameter of the "step" function is the information about time passed from the beginning of a simulation.

Another function defined for each agent is the function "die". It kills the agent and removes it from a simulation. The exact behavior of that function depends on the current execution mode and is described later. Agents can change their own state variables. If an agent wants to change some variables of another agent, it can do so directly, but this is not recommended. If an agent changes variables of another agent, it can create inconsistencies in a parallelized environment. Agents can change states of other agents indirectly.

For example, an agent can change some value in a data layer or a global variable and this, in turn, will change the state of other agents. Agents may read the state of another agent, though care should be taken in the case of parallelized simulation, since several agents that read the same variable of another agent during a simulation step can get distinct values depending on the time when the variable was read.

Links are special agents that can connect two other agents, so that each agent knows to which other agents it is connected. Links are agents, so they have the "step" function and they have specific behavioral rules. One class of links is the "SpaceLink" which can be used to connect SpaceAgents (which are described later) in a space. SpaceLinks have a special function that returns its length, e.g., the distance between two connected agents.

One particular example of a link is a model for a physical spring that connects two agents. In this case, the behavior of a link (spring) is the application of forces to connected agents if the length of the link (spring) has been changed. For instance, in vascular tissues, smooth muscle cells are normally attached to each other, which can be simulated by these physical springs. We can adjust the spring coefficient and the rest length of the spring to fit the desired behavior of smooth muscle cells. When there are forces applied to these smooth muscle cells, these springs may change their lengths and also generate forces against the original force. In this case, we would be able to see the dynamic changes of smooth muscle cells under internal and external forces.

A space is a structure which groups SPARK agents based on their positions. Each SPARK model may contain several spaces with different properties; however, one "base" space needs to be defined as the default space for that model. A space facilitates interactions between agents, and provides additional organization and structure for their interactions. It is not required for an agent to exist in a space; it is possible to define agents that have no spatial properties. Examples of such agents include those that modify values in a data layer at each simulation step, or those that collect some statistics.

Agents that can exist in a space are derived from a SPARK class called "SpaceAgent". All SpaceAgents can freely move in a space where they are located, and they can change their size and shape. When a new SpaceAgent is created, it is automatically put into the default space of a model. Any SpaceAgent should be located in only one space at one time step, but they can move from one space to another.

Technically, SpaceAgents are not directly contained inside a space. Instead, each Space-Agent contains a variable of type "SpaceNode", which associates an agent and a space. In other words, SpaceAgents are attached to SpaceNodes, and SpaceNodes are entities that exist in a space. A SpaceNode contains all information about "physical" appearance of an agent in a space, such as its coordinates, size and shape. An agent can be thought of as a brain that controls a body (SpaceNode). This approach allows changing SpaceNodes for an agent dynamically. For instance, all SpaceNodes have a fixed shape, and if an agent wants to change its shape, then it is enough to create a new SpaceNode that has a desired shape and attach an agent to this new node. There are circular SpaceNodes, square SpaceNodes; this is done for efficient collision detection algorithms. Each space has some topological structure. It is not required to have a Euclidean coordinate system in a space, but in the current version of SPARK only Euclidean spaces are available. There are two main types of spaces in SPARK: a continuous space and a grid (discrete) space. Each type can be either two-dimensional or three-dimensional. The basic topologies of these spaces are rectangular, cylindrical, or toroidal.

A continuous space has the usual Euclidean coordinate system. In a grid (discrete) space, some operations have special meaning. A grid space is divided into cells—squares in a two-dimensional space, cubes in a three-dimensional space—and all agents in the same cell are considered to be at the same location on the grid. There are several operations available in a space itself. One can get all agents at a specific location, get all agents of a given class at a specific location, or all agents that overlap with another specified agent type. Using space allows for more efficient operation than iteration over all agents. Other operations in space include getting space size and space topology.

Data layers are used to define a scalar field in a space. A data layer associates a numerical value with each point of a space, making it easy to work with these values and to perform operations on them. Data layers can be implemented in different ways. The simplest way is to define a grid structure in the bounded space. Each cell of the grid keeps some numerical value, and all points in the space inside this cell are associated with this value. Computations involving grids can be performed quite efficiently since each grid stores numeric values in a rectangular table.

The data layers can be used to represent the location specific values which can have smaller scale than agents. For example, if agents represent cells and a space represents a tissue then data layers represent chemical compounds in the tissue. In SPARK, data layers can be of different scale. Some data layers can be coarse, other can be fine. Each data layer is associated with one space for which the data layer is defined. Each space contains a complete list of all data layers inside it. SpaceAgents can read and change values of any data layer at any position of a space. In particular, it is common to work with data layers at the location of an agent itself. There are special operations defined for data layers which allow reading and modifying values at the location of a specific agent. Reading and changing values at a specific point of a data layer are local operations for a data layer.

Global operations defined for data layers include diffusion and evaporation. There are two implementations of a diffusion operation in SPARK. One is a simple diffusion (similar to NetLogo), which diffuses a value of a data layer cell to all adjacent neighbors. Another version of a diffusion operation is an improved version of a simple diffusion that allows diffusion to all neighbors at a specific distance. Evaporation implements degradation of the value of a data layer at the specified location.

The Observer has two main functions: it is the main container for all other SPARK components and it schedules and executes actions of other components. Agents and spaces are contained directly in the Observer. Basic functions of the Observer allow retrieval of information about created agents (for example, a number of agents of a given class) and sets of agents. When a new agent is created it is automatically added to the Observer. When an agent dies, it is removed from the Observer. The Observer also can be used to get information about spaces defined in a model; data layers are stored in spaces, so to get information about a data layer, it is required to get space first, and then retrieve a data layer.

There are two main modes in which the Observer executes actions of agents. The first mode is called the serial mode. In this mode, agents carry out their steps one after another and all actions of agents have an immediate effect. For example, if an agent hatches another agent, then the hatched agent is immediately added to the set of existing agents and all other agents are able to see it. The second operation mode is called the concurrent mode. In this mode, many actions of agents are postponed until the end of a simulation step, and executed only after all agents have made their steps. For instance, if the Observer runs in the concurrent mode, then a newly created agent will not be added to the set of agents immediately. It will be added only after all agents finish their steps. The main idea of the concurrent mode is to make the order of agents' actions irrelevant. This mode is particularly useful for implementation of a parallelized version of SPARK because it prevents synchronization problems. In many cases no changes are required for a serial model to be able to run in the concurrent mode.

The Observer also schedules agent actions. The scheduler works at the level of agent classes, so agents of the same class are scheduled in the same way. The basic operation of the scheduler is to specify at which simulation steps agents of a particular class will act. For example, if some agents can act at each simulation step, while others only each third step, a convenient way to schedule actions is by using the notion of simulation time. In this case each simulation step has a time value associated with it; therefore each simulation step represents the smallest unit of time for the simulation. For each agent class, it is possible to define the time interval between actions of agents of that class. For instance, there could be agents who act after two time units and agents who act after one and half time units (fractional time is also possible). Then, a simulation will proceed as follows: nobody will act during the first simulation step, agents of the second type (one and half time units) will act during the second simulation step, agents of the first type will act during the third simulation step, and after them agents of the second type will also act (three time units passed), etc. Besides time, agents are assigned priorities. If there are several agents acting at the same time point, priority tells the Observer which agent will act first. If no priority is specified explicitly, or if two agents have the same priority, then lexicographic order on agent class names determines the order of agents' actions.

The SPARK programming language (SPARK-PL) was developed to simplify the process of model creation by researchers not experienced in computer programming. Its syntax is derived primarily from the Logo programming language (the inspiration for NetLogo language) and the Java™ programming language. All models written in SPARK-PL are translated into Java™ source code first, and then a Java™ compiler is used to produce the byte code that can be executed by the SPARK simulation engine. Because of this two-step process, it is convenient to extend SPARK-PL with native Java™ constructions. As a result, SPARK-PL harnesses the full power of the Java™ language for ABM development. The main features of this language include object oriented constructions, a static type system with type inference, close ties with SPARK, as well as the concise and expressive syntax of the Logo language.

SPARK-PL includes several object-oriented concepts such as classes and inheritance similar to mainstream general purpose programming languages (such as C++, Java™, C#). These hierarchical properties allow for greater ease of organization and scheduling code blocks, which facilitates the development of complex, large-scale models. The source code of each model in SPARK-PL can be separated into several files, and can also be easily organized in a hierarchical format.

SPARK-PL static type system eliminates many programmers' errors concerning an incorrect use of variables of incompatible type. Type inference feature of the SPARK Language makes it possible to implement models in a way similar to Logo-like languages, such as Netlogo, in which dynamic type system is used. With type inference, it is not required to provide an explicit type for every new variable. The translator is capable of finding the correct type of many variables automatically by looking at the expressions. Another advantage of static type system is that it leads to efficient and fast code, because it is not required to check type consistency in runtime (Solovyev, A, et al. SPARK: A Framework for Multi-Scale Agent-Based Biomedical Modeling International Journal of Agent Technologies and Systems, 2(3), 18-30, July-September 2010).

SPARK is implemented in the Java™ programming language. SPARK code can run on all machines with Java™ Standard Edition runtime environment version 1.5 or 1.6. The SPARK source code is freely available and can be retrieved from the SPARK repository. The compiled SPARK packages, along with the tutorials, can be downloaded from the official SPARK website. There are several third-party libraries used in SPARK: 1) JFreeChart; 2) Java™ OpenGL (JOGL); and 3) Colt. JFreeChart is used for creating and visualizing line plots and histograms in real time. JOGL is used for visualization of a simulation. Colt is a library for high performance scientific and technical computing in Java™.

According to one embodiment of the methods described herein, a system and a computer-implemented method of modeling progression of hepatic inflammation, fibrosis and cancer in a patient are provided. Generally-speaking, the method comprises first defining an agent-based model (ABM) in accordance with obtained data, the ABM adapted to simulate hepatic tissue, the ABM comprising agent data, global data, initialization process data, or any combination thereof. The agent data, global data, initialization process data, or any combination thereof comprises representations of biological elements of liver inflammation, fibrosis and cancer, for example chosen from hepatocytes, macrophages (e.g., Kupffer cells), stellate cells, and cancer cells and measurable factors relating to liver inflammation, fibrosis and cancer chosen from TNF-$\alpha$, TGF-$\beta$1, and HMGB1. The defining step includes entering agent data, global data, initialization process data, or any combination thereof into the ABM that acts as an initial state of the simulation. Next, the method comprises simulating the ABM. The simulation may be run a fixed number of cycles to represent a passage of a defined time period. Lastly, the method comprises generating output data, representing simulated hepatic conditions at one or more time points, such as hepatic tissue structure, hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof. The output data for any one or more time point may be stored on computer readable media. The simulating step may be run multiple (two or more) times to generate a stochastic range of multiple different simulation outputs, given the stochastic nature of the model. Initial values for the agent data, global data, initialization process data, or any combination thereof may be altered, or additional values added to match outcomes obtained from a patient, in order to predict an outcome for another patient for whom only partial knowledge of certain parameters or dynamics (i.e. time-dependent changes in relevant, measurable variables) are known. Likewise, initial values for the agent data, global data, initialization process data, or any combination thereof may be altered, or additional values added in order to simulate the impact of an active agent (e.g., a drug or other physiologically-active substance).

The model may comprise a therapeutic or diagnostic agent as agent data, global data, initialization process data, or any combination thereof in order to simulate the action of that agent in the simulation. By accurately simulating the impact of such an agent on a biological system, much of the cost, time, labor and resources, such as laboratory animals involved with early-stage research can be avoided by the in silico modeling. Thus, the model can simulate the impact of a therapeutic strategy for a disease or condition involving the interrelations among hepatic inflammation, fibrosis/cirrhosis, and cancer. In another non-limiting embodiment, the model is used to rationally design a drug, device, diagnostic, prophylaxis, or therapeutic strategy for a disease or condition involving the interrelations among hepatic inflammation, fibrosis and cancer. In yet another embodiment, the method is used in the diagnosis of a disease involving the interrelations among hepatic inflammation, fibrosis/cirrhosis, and cancer.

An ideal therapy for inflammation-based cancer should suppress excessive anti-inflammatory responses (which promote cancer growth) while enhancing the production of cytokines and other factors that promote pro-inflammatory responses (which promote cancer apoptosis and death). This therapy would not over-induce the pro-inflammatory response, so that bystander tissue damage could be minimized.

According to one embodiment of the methods and systems described herein, an agent-based computer simulation of the progression of hepatocellular carcinoma (HCC) is provided, including and dependent on pro- and anti-inflammatory responses present in chronic infections such as Hepatitis C virus (HCV). These simulations were calibrated on published literature data regarding the dynamics of cell populations and cytokines and their influence on inflammation and the early stages of cancer caused by chronic infection. The ABM could reproduce acute inflammation that leads to a normal healing response as well as HCC following a chronic inflammatory response, including features such as a hypoxic core and tumor angiogenesis.

One use of the ABM leverages the fact that this type of simulation can often reproduce a visual pattern of cells and tissue architecture, which in turn can be compared to a photomicrograph of a biopsy specimen from a patient or an experimental animal. Moreover, since the ABM recapitulates a biological process, additional information such as distribution of given molecules (e.g. inflammatory cytokines, pro-fibrotic molecules, or cancer-related molecules) can be depicted. These simulated patterns are comparable to those patterns seen upon immunostaining of tissue sections for such molecules. The patterns observed in the ABM simulations are derived from simulated biological processes, and thus calibrating the ABM for the pattern observed in actual photomicrographs or immunostained tissue sections can yield a quantitative prediction (in both time and levels of cells/mediators) that essentially leads to a patient-specific, personalized simulation of the inflammation, fibrosis and/or cancer process. In addition, this mechanistic foundation of the simulation means that simulated therapies can be run in silico on a patient-specific basis. Thus, this platform allows for a "smart diagnostic", which not only can lead to better prediction of the course of disease, but that can also be used to suggest specific therapeutic options.

Because these simulations include a central role for molecular surrogates of tissue damage/dysfunction, any simulated therapy can be simultaneously evaluated both for efficacy (killing tumor cells) and for safety (not inducing higher levels of damage). For example, the ABM can simulate the behavior of both standard liver macrophages (Kupffer cells) as well as tumor-infiltrating macrophages (TAM, which are known to be subverted by the tumor environment in a manner that ultimately promotes tumor growth and metastasis; A. Yuan, J. J. Chen, and P. C. Yang. Pathophysiology of tumor-associated macrophages. Adv. Clin. Chem. 45:199-223, 2008). The ABM has demonstrated the importance of TAM in the process of inflammation and early cancer and suggested that drugs targeting TAMs may be a promising therapeutic strategy (in support of prior studies; I. J. Fidler. Macrophages and metastasis—A biological approach to cancer therapy: Presidential address. Cancer Res. 45:4714-4726, 1985).

The biology encompassed in this ABM spans the range from acute HCV infection through chronic HCV infection to cancer, but can also simulate inflammation induced by non-infectious means, leading to liver fibrosis and cirrhosis. Thus, novel therapies can be explored in these settings, either on a patient-specific basis or as an in silico clinical trial. As an example, of such a therapy, the ABM is used to reproduce the anti-TNF-α antibody treatment known to be therapeutically relevant in a mouse model of ethanol-induced hepatic necrosis and inflammation (see, e.g., limuro, Y., et al., Antibodies to tumor necrosis factor alfa attenuate hepatic necrosis and inflammation caused by chronic exposure to ethanol in the rat. Hepatology, 1997. 26(6): p. 1530-7).

Another use of this ABM lies in its ability to predict novel therapeutic regimens directed at preventing the formation of cancer or treating an early-stage cancer. Simulations can be run in a state in which pre-existing cancer is assumed. In this simulation, anti-inflammatory responses precede a large decrease in pro-inflammatory responses, which drives damage/dysfunction and leads to death of the patient. Death in this model occurs not from the cancer itself, but from damage related to the dramatic increase in the inflammatory response.

This is a realistic clinical outcome. The time until patient death is inversely related to the initial cancer load. In addition, higher damage rates result in a faster progression to death along with smaller tumor size at the time of death. Thus, this model may be of use in determining the responses of patients who have had a tumor for several years.

The in silico methods would therefore be useful both for diagnosing the state of HCC (in combination with digital pathology specimens), for elucidating mechanisms of HCC treatment, for testing the effects of known therapies in the setting of HCC, and for developing novel therapies for HCC.

The modeling systems described herein comprise any number of: agent data, global data, initialization process data, or any combination thereof, within the program, representing cells, structures, proteins, chemicals, etc. In the model for hepatic inflammation, fibrosis and cancer (e.g., HCC), a computational simulation of the key inflammatory events triggered by hepatitis C viral infection was developed. The model probabilistically leads to a chronic condition, subsequently resulting in smoldering necrosis and fibrosis, an environment fertile for the progression of HCC from a few initial progenitor cells (transformed hepatocytes or cancer stem cells).

In the model, virus infects healthy hepatocytes; this injury activates resident Kupffer cells to produce pro-inflammatory cytokines such as TNF-α, and anti-inflammatory cytokines such as TGF-β1. TNF-α causes acceleration in the death of injured hepatocytes, but also has a bystander effect on local healthy hepatocytes. TNF-α also activates stellate cells, which transform into fibrosis promoting myofibroblasts, which further proliferate and increase collagen formation in response to TGF-β1.

One element of the model is a class of molecules known as alarmins or damage-associated molecular pattern (DAMP) molecules. Commonly found in the setting of runaway inflammation induced cell death, DAMPs can cause inflammatory responses to persist, even when the original pro-inflammatory stimulus has been cleared subsequent to the actions of TH1 cytokines. One such DAMP, HMGB1 (also, HMG-1), particularly in conjunction with its receptor for advanced glycation endproducts (RAGE), has been associated with the proliferation and metastasis of many tumor types. RAGE expression is elevated in hepatitis, and even more so in HCC. As such, HMGB1 is included in the hepatic inflammation and HCC models. HMGB1 protein is an abundant component of all mammalian nuclei, and related proteins exist in all eukaryotes. HMGB1 binds with high affinity to specific DNA structures such as bent or kinked DNA. It is considered to be a structural protein of chromatin. Activated macrophages and monocytes secrete HMGB1 as a cytokine mediator of inflammation. Antibodies that neutralize HMGB1 confer protection against damage and tissue injury during arthritis, colitis, ischemia, sepsis, endotoxemia, and systemic lupus erythematosus. The mechanism of inflammation and damage is binding to TLR4, which mediates HMGB1-dependent activation of macrophage cytokine release. This positions HMGB1 at the intersection of sterile and infectious inflammatory responses (see, e.g., Lotze, M. T., Tracey, K. J. High-mobility group box 1 protein (HMGB1): nuclear weapon in the immune arsenal. *Nature Rev. Immun.* 5: 331-342, 2005).

In terms of the liver structure, all or part of which can be included as elements of an ABM, sheets of connective tissue divide the liver into thousands of small units called lobules. The hepatic lobule is the structural unit of the liver. It consists of a roughly hexagonal arrangement of plates of hepatocytes radiating outward from a central vein in the center. At the vertices of the lobule are regularly distributed portal triads, containing a bile duct and a terminal branch of the hepatic artery and portal vein. Another basic unit of liver structure is the hepatic acinus, which represents a unit that is oriented around the afferent vascular system.

The parenchymal cells of the liver are hepatocytes. Hepatocytes are the chief functional cells of the liver. Roughly 80% of the mass of the liver is contributed by hepatocytes. These polygonal cells are joined to one another in anastomosing plates, with borders that face either the sinusoids or adjacent hepatocytes. The ultrastructure appearance of hepatocytes reflects their substantial metabolic role, with abundant rough and smooth endoplasmic reticulum, and Golgi membranes. Glycogen granules and vesicles containing very low density lipoproteins are readily observed. Hepatocytes contact blood in sinusoids, which are distensible vascular channels lined with highly fenestrated endothelial cells and populated with phagocytic Kupffer cells. The space between endothelium and hepatocytes is called the Space of Disse which collects lymph for delivery to lymphatic capillaries.

Kupffer cells, also known as Browicz-Kupffer cells and stellate macrophages, are specialized macrophages located in the liver lining the walls of the sinusoids that form part of the reticuloendothelial system (RES) (aka: mononuclear phagocyte system). Kupffer cells activation are responsible for early ethanol-induced liver injury, common in chronic alcoholics. Chronic alcoholism and liver injury deal with a two hit system. The second hit is characterized by an activation of the Toll-like receptor 4 (TLR4) and CD14, receptors on the Kupffer cell that internalize endotoxin (lipopolysaccharide or LPS). This activates the transcription of pro-inflammatory cytokines (Tumor necrosis factor-alpha or TNF-α) and production of reactive oxygen species such as hydroxyl radical, superoxide, and hydrogen peroxide (a pro-oxidant). TNF-α will then enter the stellate cell in the liver, leading to collagen synthesis and fibrosis. Fibrosis will eventually cause cirrhosis, or loss of function of the liver.

Hepatic stellate cells (stellate cells), also known as perisinusoidal cells or Ito cells (earlier lipocytes or fat-storing cells), are pericytes found in the perisinusoidal space (a small area between the sinusoids and hepatocytes) of the liver also known as the space of Disse. The stellate cell is the primary cell type involved in liver fibrosis. Stellate cells can be selectively stained with gold chloride, but their distinguishing feature in routine histological preparations is the presence of multiple lipid droplets in their cytoplasm. Reelin also is a marker in discerning them from other myofibroblasts, which is increasingly expressed after liver injury. In normal liver, stellate cells are quiescent and represent 5-8% of the total number of liver cells. When the liver is damaged, stellate cells are activated and are characterized by proliferation, contractility, and chemotaxis. Activated stellate cells also are responsible for secreting collagen scar tissue, which can lead to cirrhosis. Cirrhosis results from chronic liver disease and is characterized by fibrosis, formation of scar tissue and regenerative nodules, and is accompanied by loss of liver function. Cirrhosis is most commonly caused by alcoholism, hepatitis B and C, and fatty liver disease, but has many other possible causes and in some cases is idiopathic.

Tumor necrosis factor (TNF-α, formerly known as cachexin or cachectin) is a multifunctional pro-inflammatory cytokine secreted predominantly by monocytes/macrophages that has effects on lipid metabolism, coagulation, insulin resistance, and endothelial function. The primary role of TNF-α is in the regulation of immune cells. TNF-α is able to induce apoptotic cell death, to induce inflammation, and to inhibit tumorigenesis and viral replication.

Figure 7:
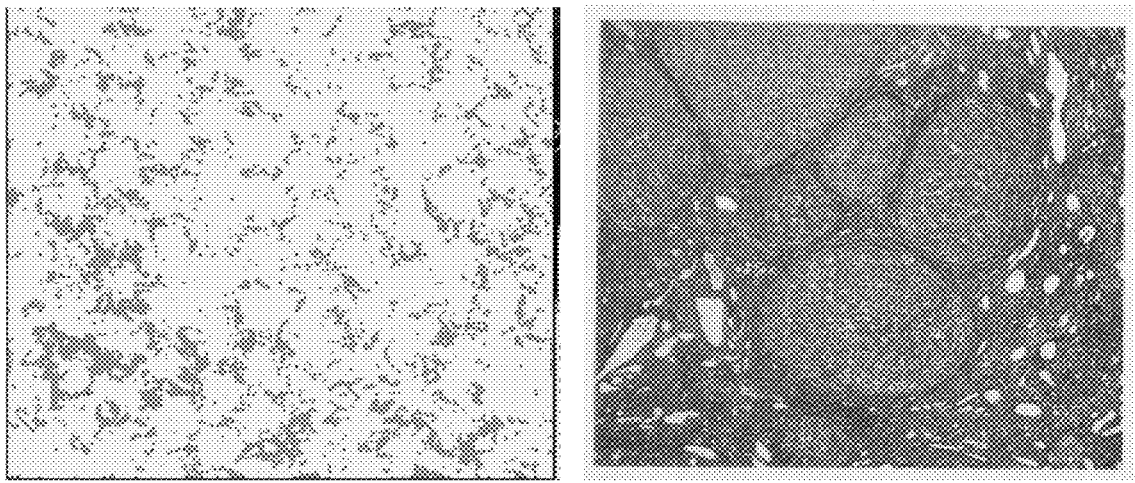
FIG. 7: Appearance of periportal and bridging fibrosis in a liver ABM (left) similar to patterns of early cirrhosis as seen clinically in Masson-Trichrome stained liver samples (right).

The emergent visual pattern of changes to the liver tissue when simulated over a course of time, for example as seen in FIG. 7, described below, provides an image to be compared to images of clinical pathology. As the ABM is stochastic, multiple runs of the same initial conditions would create diverse outcomes.

Thus, according to one embodiment of the systems and methods described herein relating to digital pathology, simulated images of liver tissue are generated that are grids representative of hepatic tissue. Digital pathology is a computer-implemented, image-based process that allow for the management of information generated from a digital slide, which is produced, for example, by scanning, analyzing and storing on computer readable medium digitized photomicrograph images, e.g., from a glass slide. Those images are compared to an image of a patient's liver tissue. Because the ABM is stochastic in nature, running the ABM multiple times results in multiple outcomes that generate representative data values, such as hepatic tissue structure, inflammation state, inflammation-induced damage, viral load, virally-induced damage, presence of a tumor, size of a tumor, presence of cancer (e.g., metastasis), size or extent of metastasis, and state of fibrosis (e.g., cirrhosis). A database of images is produced and is stored in computer storage. By comparing an image of a liver biopsy of a patient with the image representations of the multiple simulation outputs in computer storage and determining a best match with the image of a liver biopsy of a patient, an output that includes a patient prognosis can be produced because each computer-generated image stored in the library is connected with a specific series of images and outcome data corresponding to each individual run of the simulation that produced the matching computer-generated image. Also, the simulation can be run using differing initial values, parameters, agents, etc. to generate additional data images for storage in the library on the computer storage. This can be of value because in many cases, liver inflammation, fibrosis and cancer is a long-term process, and earlier exposure to one of many factors that can alter the simulation, whether known or unknown, to a patient. Thus the model also comprises both 1) simulating the ABM multiple times such that multiple different simulation outputs comprising a plurality of image representations of the grid for the plurality of time points are generated, and storing the image representations of the multiple simulation outputs on a computer readable medium (e.g., in a database) and 2) altering the agent data, global data, initialization process data, or any combination thereof from its original states and simulating the ABM multiple times such that multiple different simulation outputs comprising a plurality of image representations of the grid for the plurality of time points are generated, and storing the image representations of the multiple simulation outputs on a computer readable medium (e.g., in a database). In either case, the systems and methods comprise comparing an image of a liver biopsy of a patient with the image representations of the multiple simulation outputs the computer readable medium and determining a best match with the image of a liver biopsy of a patient; and producing an output that includes a patient prognosis based upon output data produced by the simulation that generated the best match image representation.

A large number of examples of image comparison software programs are available. Examples include: Image Comparer (Bolide Software, Russian Federation), Perceptual Image Diff, Imatch3 (Photools); and IRMA ((Image Retrieval in Medical Applications, Aachen University of Technology, Aachen, Germany, an example in which this is used in a clinical environment. See also Hipp et al., as an example of paper showing implementation of image comparison in the pathology setting (Spatially Invariant Vector Quantization: A pattern matching algorithm for multiple classes of image subject matter including pathology *J Pathol Inform* 2011, 2:13).

As described above, all of these methods can be simulated by modeling on a computer system. Thus, also provided is system for modeling progression of at least one hepatic condition. The system comprises on at least one computer with a computer readable medium having programming instructions stored thereon, which, when executed by a processor of the at least one computer, cause the processor to: a) receiving or defining at least one of the following: agent data, global data, initialization process data, or any combination thereof, the agent data comprising at least one of the following: definition data, behavior data, class data, internal state data, function data, link data, space data, or any combination thereof; b) modeling the at least one hepatic condition associated with at least one agent based at least in part upon at least a portion of the agent data corresponding to the at least one agent; and c) generating modeling output data representative of at least one of the following: hepatic tissue structure, hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof. The system may further comprise modeling the at least one hepatic condition multiple times to generate multiple different modeling output data, which can be stored on computer readable medium, e.g., in a database. The system may comprise output data from altering agent data, global data, initialization process data, or any combination thereof and modeling the at least one hepatic condition multiple times to generate multiple different modeling output data, which can be stored on computer readable medium, e.g., in a database. Examples of altering agent data, global data, initialization process data, or any combination thereof include, changing a value for one or more agents of the model, adding an additional agent to the model, etc., representing such biological elements such as viral load, type of virus, blood levels of one or more proteins, damage to the liver, inflammatory state, tumor size, vascularization of a tumor, surgical removal of a tumor, the effects of a cytotoxic drug, such as the simulated death of both tumor cells and hepatocytes, the effects of an antiviral drug, such as viral killing combined with increased inflammation, the effects of an anti-inflammatory drug, such as reduction in inflammation and inflammatory damage, immunosuppression and increased viral growth, the effects of an anti-fibrotic drug, such as a reduction in fibrosis, increased inflammatory damage and suppression of tissue healing, etc.

In one embodiment, the output data comprises a simulation of liver tissue on a grid for a plurality of time points and in one further embodiment comprises storing images representative of the grids on computer readable medium, e.g., in a database. As indicated above, a patient's prognosis or an outcome based on a therapeutic regimen may be determined by modeling the at least one hepatic condition multiple times using the same or different agent data, global data, initialization process data, or any combination thereof, to generate multiple different modeling output data comprising a plurality of image representations of the grid for the plurality of time points, which are stored on a computer readable medium. An image of a tissue sample from a liver biopsy can then be compared to the stored image representations of the grid in order to identify a best match—that is, an image in the database of stored images that best matches that of the image of the tissue sample. Because the stored image representations of the grid are representations taken from different time points in specific individual runs of the modeling step, a patient's prognosis can be determined and output by looking at output data for later time points in the particular run of the modeling step.

A method of modeling progression of at least one hepatic condition also is provided. The method is performed on any system as described above and comprises, in the at least one computer, receiving or defining at least one of the agent data, global data, initialization process data, or any combination thereof; modeling the at least one hepatic condition; and generating output data from the modeling step representative of at least one of the following: hepatic tissue structure, hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof. According to one embodiment, the method is performed on at least one computer with a computer readable medium having programming instructions stored thereon, which, when executed by a processor of the at least one computer, cause the processor to: a) receive or define at least one of the following: agent data, global data, initialization process data, or any combination thereof, the agent data comprising at least one of the following: definition data, behavior data, class data, internal state data, function data, link data, space data, or any combination thereof; b) model the at least one hepatic condition associated with at least one agent based at least in part upon at least a portion of the agent data corresponding to the at least one agent; and c) generate modeling output data representative of at least one of the following: hepatic tissue structure, hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof.

Example 1

Figure 4:
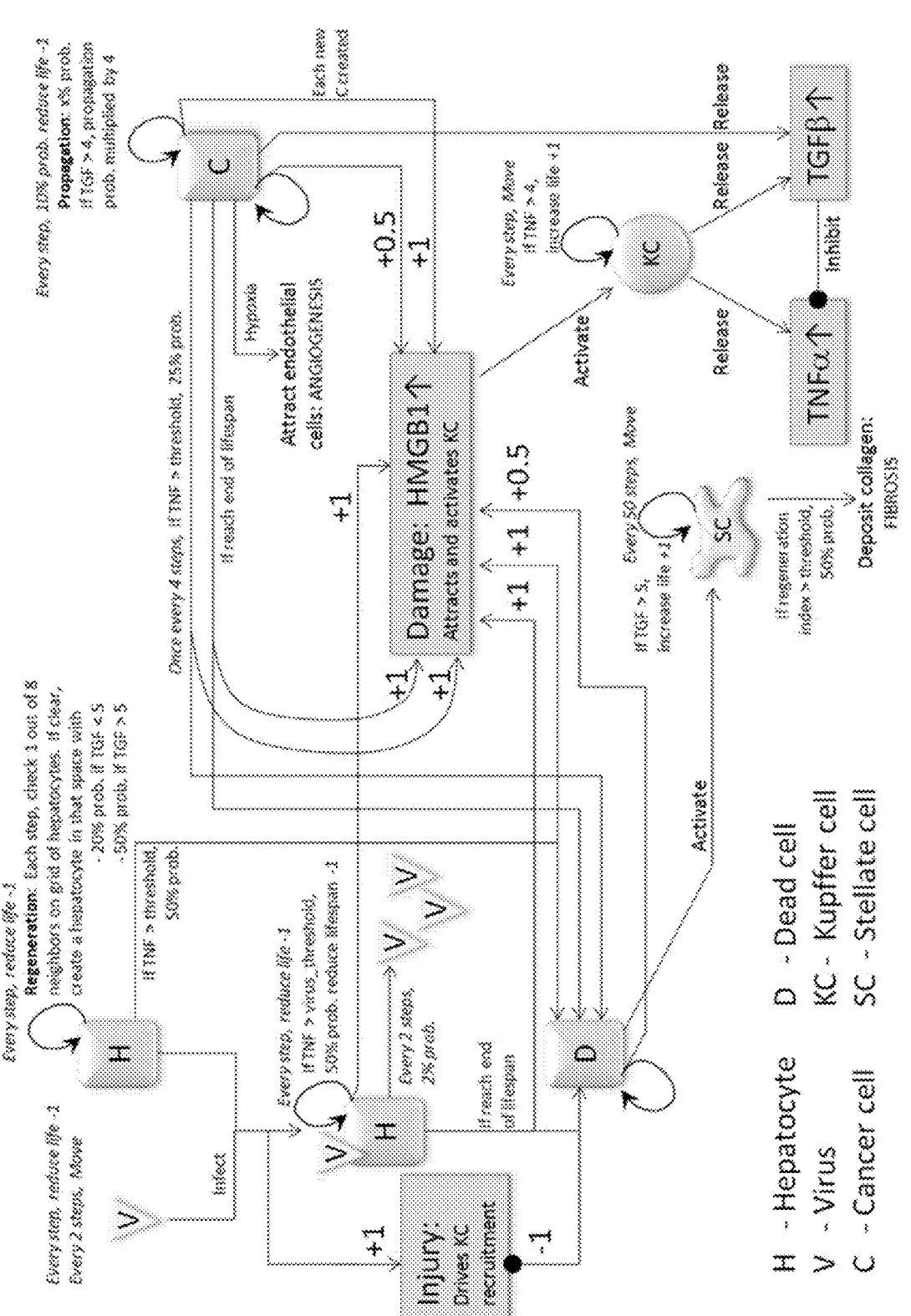
FIG. 4 is a flow diagram showing the inter-relationship of elements of the SPARK-implemented ABM described in Example 1.

The following are the rules created for the agent data, global data, initialization process data, or any combination thereof (agents, layers, etc. depicted in FIG. 4).

Time scale. It was assumed in the model that one unit of simulated time represents 0.21 days. This assumption results in the rise and fall of virally-driven damage levels, from initiation to resolution, in approximately 6 weeks. The dynamics of cell behavior and cytokine production and decay were calibrated proportionately towards this time course.

Initialization. The model begins with 200×200 cell grid representing a small portion of liver tissue. The cell types present in this liver tissue at baseline are hepatocytes (the main structural and functional cell of the liver), Kupffer cells (the resident macrophages [inflammatory cells] of the liver), stellate cells (cells that can drive the healing of the injury and are key players in fibrosis), cancer cells (which start as clonal progenitors or "cancer stem cells"). Portal triads (afferent liver blood vessels) are present in a regular grid among the hepatocytes, forming the vertices of hexagonal lobules grouping the hepatocytes. These portal triads form the baseline circulatory system providing nutrients to healthy liver tissue, and also provide the entry point to the liver for the blood-borne virus. The portal triads are connected by a thin layer of connective tissue comprising the border of each lobule, and a data layer with constant diffusion gradient implements zonal differentiation (Zones 1-3) for hepatocytes based on their distance from border to the center of a lobule, with a graded decrease in oxygenation levels towards the center of the lobule. The cell types and interactions are shown in Table 1, along with the initial values relevant to this particular example. When infected with virus, the initialization value is the number of viruses randomly dispersed in the simulated liver tissue slice. Only the virus whose location coincides with a portal triad survives (dispersal function), thus implementing the blood vessel into the liver as the site of infection, as well as stochastically setting the number of initial virus that arrive at the liver alive. Lifespans of the various cells and viruses are set to a baseline constant plus a random number within a specified range. Cytokines, represented as data layers, are the pro-inflammatory TNF-α (TNF), anti-inflammatory TGF-β1 (TGF) and the damage-associated molecular pattern molecule/danger signal High Mobility Group Box 1 (HMGB1). Each of these are initialized to 0, are only produced by agents subsequent to certain activity, and are subject to steady diffusion (fraction of the value in this grid location divided between neighbors) and degradation (fraction of the value in this grid retained) rates. Another data layer, Oxygen, is representative of oxygenation from the portal triads permeating surrounding tissue. A global parameter for Injury is also tracked.

TABLE 1

| Initialization of the Model | |
|---|---|
| | Initialized to |
| Number of Cells created | |
| Resident macrophages (Kupffer cells) | 50 |
| Resident stellate cells | 50 |
| Viruses | 500 * 20, subject to dispersal function |
| Cancer cells | 4 |
| Lifespan | |
| Hepatocyte lifespan | $100 + x$, where $0 < x < 500$ |
| Virus lifespan | $5 + x$, where $0 < x < 15$ |
| Macrophage lifespan (begins after activation) | $50 + x$, where $0 < x < 50$ |
| Stellate lifespan (begins after activation) | $5 + x$, where $0 < x < 20$ |
| Cancer cell lifespan | $1000 + x$, where $0 < x < 50$ |
| Rates | |
| Virus proliferation rate | 15 |
| Cancer propagation probability | 0.02 |
| Macrophage activation probability | 1 |
| Stellate activation probability | 0.04 |
| Thresholds | |
| Bystander TNF threshold | 4 |
| Tumor TNF threshold | 4 |
| Virus TNF threshold | 4 |
| Data Layers | |
| TNF (TNF-α) | 0 |
| TGF (TGF-β1) | 0 |
| HMGB1 | 0 |
| Oxygen | 3 per Portal triad position |
| Diffusion Rates | |
| TNF | 1 |
| TGF | 1 |
| HMGB1 | 1 |
| Oxygen | 1 |
| Degradation Rates | |
| TNF | 0.92 |
| TGF | 0.95 |
| HMGB1 | 0.9 |
| Oxygen | 0.996 |

Rules governing the model are shown in Table 2. At each time step, an agent takes action based on specified rules of behavior.

TABLE 2

| Rules governing the Model | |
|---|---|
| Agents | Rules |
| Hepatocyte | Stationary, no motion. |
| | Check value of TGF at grid position. |
| | If TGF > 5, |
| | With 50% probability: |
| | Check 1 of its 8 neighboring spaces to see if there is free space, and create a new hepatocyte there |
| | Else |
| | With 20% probability: |
| | Check 1 of its 8 neighboring spaces to see if there is free space, and create a new hepatocyte there |

TABLE 2-continued

Rules governing the Model

| Agents | Rules |
|---|---|
| | Check value of TNF at grid position. |
| | If TNF > Bystander TNF threshold, |
| | With 50% probability: |
| | Convert Hepatocyte to Dead cell |
| Infected | Raise HMGB1 at this grid position by 1 unit |
| (Subtype of | |
| Hepatocyte) | If Infected hepatocyte, |
| | Raise HMGB1 at this grid position by 1 unit |
| | Check value of TNF at grid position. |
| | If TNF > Virus TNF threshold, |
| | With 50% probability: |
| | Reduce lifespan by an additional unit |
| | Release virus (replication within infected hepatocyte) |
| | periodically (every $2^{nd}$ step) |
| | with 1% probability |
| | number = random within the range |
| | [virus-proliferation rate ± 2] |
| | If reach end of lifespan, |
| | Convert Infected hepatocyte to Dead cell |
| | Raise HMGB1 at this grid position by 1 unit |
| | Reduce Injury at this grid position by 1 unit |
| Dead | If Dead cell, |
| | Raise HMGB1 at this grid position by 0.5 unit |
| Virus | Motion: Stochastic walk |
| | If Hepatocyte present at this grid position, |
| | Convert it to Infected hepatocytes |
| | Raise Injury at this grid position by 1 unit |
| Macro- | Always activated |
| phage | Motion: Stochastic walk chemoattracted by HMGB1 |
| | Baseline replenishment of resident macrophages |
| | (Kupffer cells): |
| | Created periodically (every step) with 50% probability |
| | number = 1 or 2 |
| | Injury-driven recruitment of circulating macrophages: |
| | Created periodically (every $5^{th}$ step), with 70% probabil- |
| | ity: |
| | number = total injury * macrophage activation probability |
| | If come in contact with a Stellate cell, activate it |
| | If come in contact with a Dead cell, phagocytose it |
| | If come in contact with an Infected hepatocyte, |
| | phagocytose it with 20% probability |
| | and reduce Injury at this grid position by 1 unit |
| | Check value of HMGB1, TNF and TGF at grid position: |
| | If HMGB1 > 0.01 |
| | [ |
| | TNF += 1/(TGF + 0.01) |
| | TGF += 0.238 |
| | ] |
| Stellate | If activated: |
| | Motion: Stochastic walk |
| | Check value of HMGB1 and TGF at grid position: |
| | If TGF > 1, increase its lifespan by 1 |
| | If HMGB1 > 1, create Fibrosis |
| Portal Triad | Raise Oxygen at this grid position by 3 units |
| | If Cancer Cell present at this grid position, then |
| | remove Portal Triad |
| Cancer Cell | Stationary, no motion. |
| | Raise HMGB1 at this grid position by 2 units |
| | Raise TGF at this grid position by 0.2 units |
| | With 10% probability: |
| | Reduce lifespan by 1 unit |
| | If reach end of lifespan, |
| | Convert Cance Cell to Dead cell |
| | Raise HMGB1 at this grid position by 3 units |
| | On every $4^{th}$ step, |
| | Check value of TNF at grid position. |
| | If TNF > Tumor TNF threshold, |
| | With 25% probability: |
| | Convert Cancer Cell to Dead cell |
| | Raise HMGB1 at this grid position by 2 units |
| | Check value of TGF at grid position. |
| | If TGF > 2, multiply propagation probability by 4. |
| | Propagation: |
| | With 50% chance of propagation probability: |
| | Check 1 of its 8 neighboring spaces to see if there |
| | no Cancer |

TABLE 2-continued

Rules governing the Model

| Agents | Rules |
|---|---|
| | Cell in that space, |
| | and create a new Cancer Cell there. |
| | Raise HMGB1 at this grid position by 1 unit |
| | On every $8^{th}$ step, |
| | With 1% probability, if Oxygen at present grid |
| | position < 1, |
| | Create Platelet (Angiogenesis at the hypoxic core of the |
| | tumor) |

The initial stage of the model begins with a 2-D view of a small patch (a few square mm) of liver tissue, about 40,000 simulated hepatocytes. Hepatocytes are arranged in hexagonal lobules, with portal triads present at the vertices, forming the baseline circulatory system providing nutrients to healthy liver tissue. They also serve as the entry point for the bloodborne virus. The portal triads are connected by a thin layer of connective tissue comprising the border of each lobule, and a data layer with constant diffusion gradient implements zonal differentiation (Zones 1-3) for hepatocytes based on their distance from border to the center of a lobule; moving from Zone 1 (periportal) to Zone 3 goes from higher to lower oxygen uptake and regenerative capacity.

Events take place in the model as an aggregate of rule-based behavior by each individual agent. Bloodborne virus arrives at the tissue via the portal triads. The number of viruses is a random function of user-provided inoculation. Infected hepatocytes act as a site of virus replication, and as they die are detected as tissue injury and damage. These factors drive activation of local Kupffer cells, which lead to further recruitment of activated macrophages and release of pro-inflammatory cytokines (such as TNF-α) and anti-inflammatory cytokines (such as TGF-β1). They also lead to activation of stellate cells, which then differentiate into myofibroblasts that ultimately drive local fibrosis. Probabilistic rules governing the biological interactions allow for stochastic outcomes that can be analyzed and compared to real clinical outcomes.

Example 2

Our model was built using an agent-based approach, which is particularly well suited to representing transition between mechanisms at a local scale of organization, to global emergent behavior. We simulate rule-based interactions between parenchymal cells, inflammatory cells and cytokines that participate in the response to HCV infection, and may drive the initiation and progression of HCC.

Figure 5:
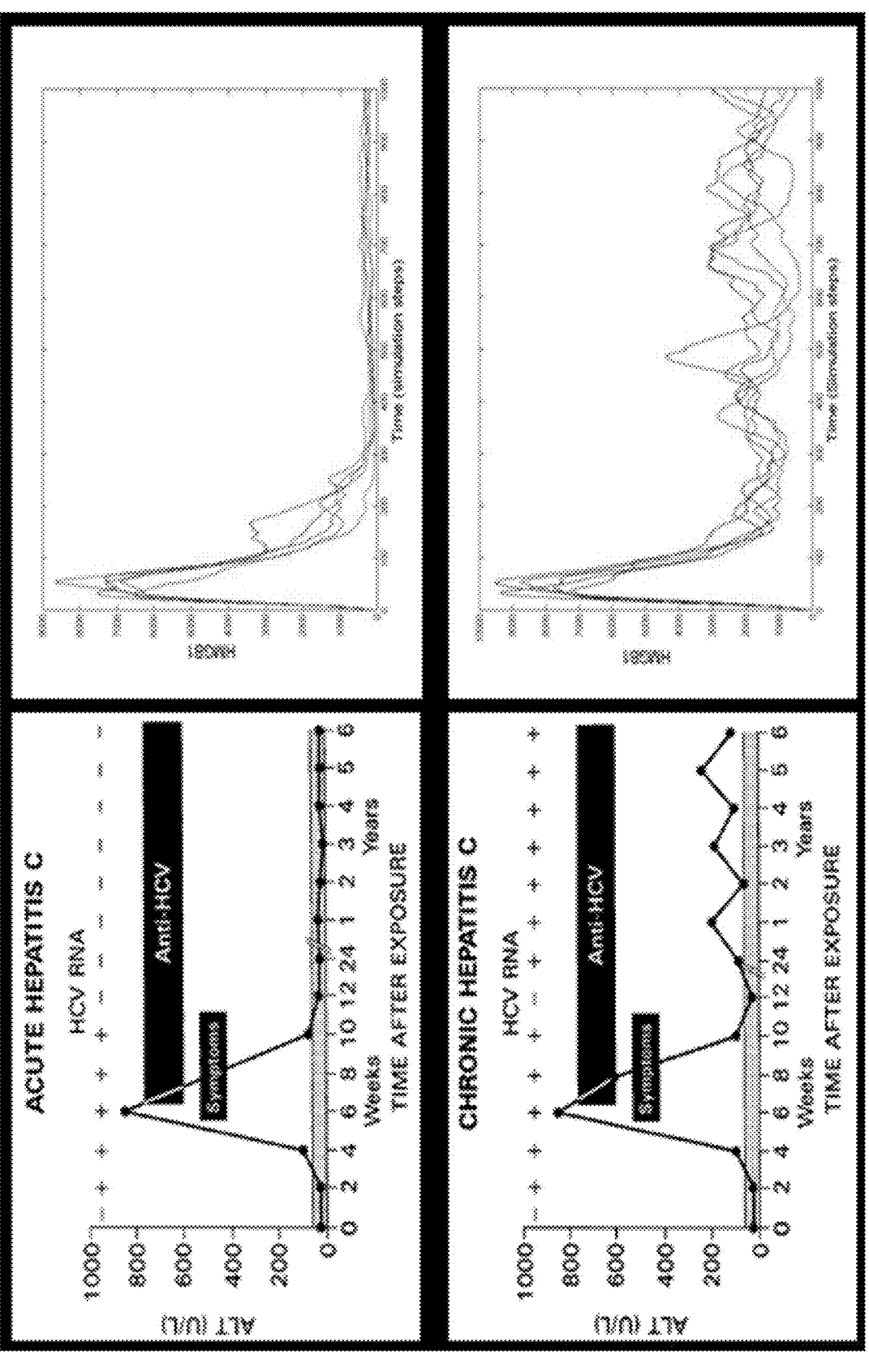
FIG. 5: Left panel: The time course of serum alanine aminotransferase (ALT) levels in a typical case of acute, self-limited hepatitis C (top) and chronic hepatitis C (bottom) [Hepatitis C: The Clinical Spectrum of Disease, Hoofnagle JH (1997) Hepatology 26(Suppl 1):155-205]. Right panel: The time course of HMGB1 levels in our simulated liver section, for several independent viral inoculations of Hepatitis C. Some instances of infection led to acute, self-limited hepatitis C (top) while others resulted in chronic hepatitis C (bottom).

One example of such emergent behavior is the course of liver damage after viral infection (FIG. 5).

Figure 6:
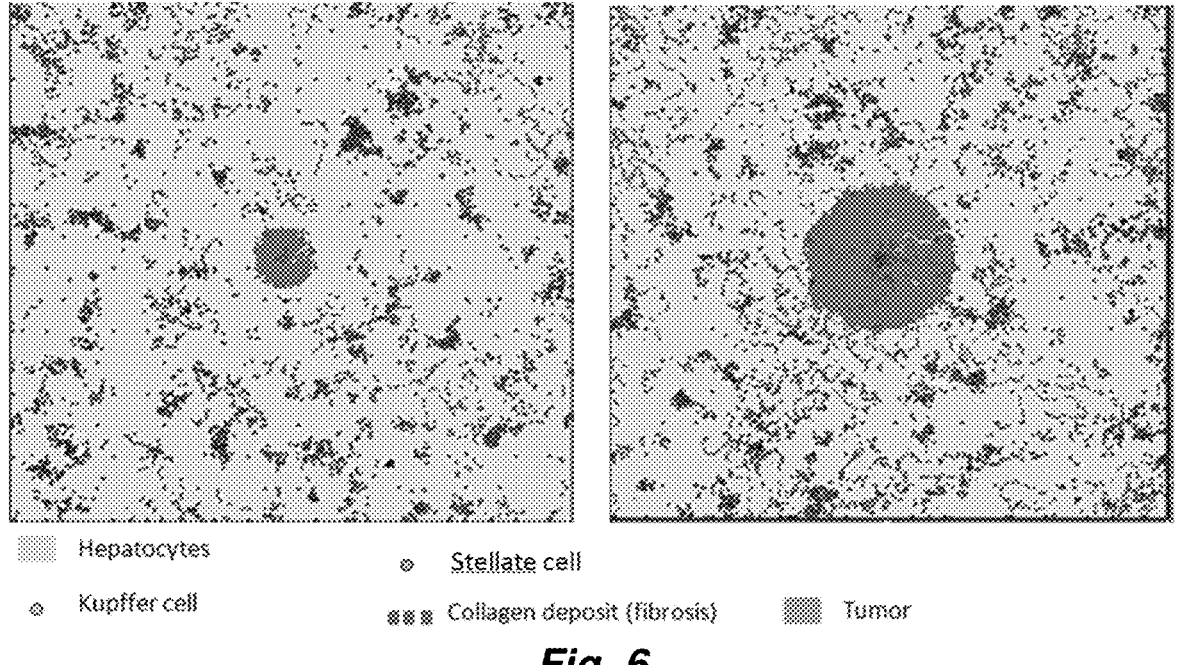
FIG. 6: Initial tumor formation (left) and progression (right) over the following 12 years in one case of chronic hepatitis C.

As the simulation progresses, SPARK provides a visual representation of changes to the area of the liver under observation, and simultaneous measurements of the number of active agents (macrophages, viruses, hepatocytes, etc.) and levels of data layers (cytokines, oxygen or other diffusible factors). An example of tracking the realtime measurements is shown in FIG. 5, Right panel. An example of the visual representation is shown in FIG. 6.

Example 3—Cirrhosis Model

Cirrhosis is a common outcome of chronic hepatitis C, and 70-90% of cases of hepatocellular carcinomas are observed in cirrhotic livers. We therefore have also been exploring the emergence of cirrhosis in this liver ABM. Myofibroblasts are chemoattracted by TGF-β, and proliferate and produce collagen in response to TGF-β. By calibrating for the influence of zonal differences on collagen production, the course of pattern formation in the development of cirrhosis—periportal fibrosis, followed by bridging fibrosis, eventually disrupting the regular lobular structure with regenerative nodules—is reproduced. (FIG. 7).

The basic structure of the model is the same as in Example 1. The differences in this example are: 1) Addition of new agents: Myofibroblast, Septa, and Collagen. These develop more structural detail for the zonal behavior relevant to the lobule. Since their creation and actions are downstream of the action of agents in Example 1, the initialization of all agents for this Example remains the same as in Example 1; 2) Calibration: Oxygen originating out of Portal triads is calibrated to have a steady gradient implementing zonal differentiation centered around the periportal area; and 3) No cancer cells were seeded, therefore there was no tumor formation in this instantiation of the model.

TABLE 3

Changes in initialization of the Model for Example 3

|  | Initialized to |
|---|---|
| Data Layers | |
| Oxygen | 0.2 |
|  | per Portal triad position |
| Diffusion Rates | |
| Oxygen Degradation Rates | 0.5 |
| Oxygen | 0.95 |

TABLE 4

Changes in rules governing the Model for Example 3

| Agents | Rules |
|---|---|
| Hepatocyte | Stationary, no motion. |
|  | Check number of Collagen units present at grid position. |
|  | If Collagen > 5 |
|  | Create Fibrosis |
|  | Check value of HMGB 1 at this grid position. |
|  | If HMGB1 > 1 |
|  | Raise TGF at this grid position by 0.2 |
| Dead | If Dead cell, |
|  | Raise HMGB 1 at this grid position by 0.1 unit |
| Macrophage | Check value of Injury, and value of HMGB1 at grid position. |
|  | Activated if HMGB1 > 0.05 or Injury > 0.5 |
|  | If activated: |
|  | Motion: Stochastic walk; chemoattracted by HMGB1 |
|  | Inactivated if Injury = 0 |
|  | If come in contact with a Stellate cell, check value of TNF at this grid position |
|  | If TNF > 1 |
|  | With probability =stellate activation probability, Transform Stellate to Myofibroblast |
| Stellate | If activated, transform to Myofibroblast (accomplished by Macrophage rule) |
|  | Unaffected by HMGB1 (unlike in Example 1) |
| Portal Triad | Raise Oxygen at this grid position by 0.2 units |
| Septa | Raise Oxygen at this grid position by 0.1 units |
|  | If Cancer Cell or Fibrosis present at this grid position, then remove Septa |
| Myofibro-blast | Always activated |
|  | If activated: |

TABLE 4-continued

Changes in rules governing the Model for Example 3

| Agents | Rules |
|---|---|
|  | Motion: Stochastic walk; chemoattracted by TGF |
|  | Check value of Oxygen and TGF at this grid position. |
|  | If Oxygen > x, where x = random within the range [0 to 2] |
|  | If TGF > 5 |
|  | Deposit 1 unit of Collagen |
|  | With 5% probability, create a new Myofibroblast |
| Collagen | If Cancer Cell or Fibrosis present at this grid position, then remove Septa |

Having described this invention above, it will be understood to those of ordinary skill in the art that the same can be performed within a wide and equivalent range of conditions, formulations and other parameters without affecting the scope of the invention or any embodiment thereof.

We claim:

1. A computer-implemented method of modeling progression of at least one hepatic condition in a patient, comprising:

(i) receiving, with at least one processor, data relating to at least one first parameter of a plurality of parameters associated with a hepatic condition in a patient, wherein the at least one first parameter is a level of at least one cytokine;

(ii) identifying, with at least one processor, at least one first rule from a rules database, the at least one first rule comprising:

(a) determining a level of the cytokine at a first position associated with at least one hepatocyte;

(b) comparing the level of the cytokine at the position with a threshold cytokine value; and (c) changing a status of a second position based on the cytokine level;

(iii) generating, with at least one processor, a simulated progression of the hepatic condition by applying the at least one first rule to the data relating to the at least one first parameter, thereby generating a progression of the hepatic condition based on the at least one first rule;

(iv) generating in a continuous space, using at least one processor and based on the simulated progression, image output providing predicted hepatic tissue structure, the image output comprising representations of one or more of hepatocytes, stellate cells, and Kupffer cells;

(v) repeating steps (i)-(iv) to generate a stochastic range of the image output of the simulated progressions, the stochastic range of image output comprising a plurality of images generated based on interactions among one or more of hepatocytes, stellate cells, and Kupffer cells based at least in part on the cytokine levels and the at least one first rule;

(vi) comparing, with at least one processor, the stochastic range of image output of the simulated progressions with one or more liver biopsy images, the comparison comprising at least a comparison of one or more hepatocytes, stellate cells, and Kupffer cells; and (vii) determining, using at least one processor and based at least on the comparing, a prognosis of the hepatic condition in the patient.

2. The computer-implemented method of claim 1, further comprising:

(viii) associating, using at least one processor, the image output corresponding to a matched liver biopsy image and storing the associated data in a database.

3. The computer-implemented method of claim 1, wherein the step of determining a prognosis further comprises diagnostic information relating to the patient.

4. The computer-implemented method of claim 1, wherein the data comprises an image of hepatic tissue and the cytokine is a pro-inflammatory cytokine.

5. The computer-implemented method of claim 4, wherein the step of generating a simulated progression of the hepatic condition comprises a step of modifying the image of hepatic tissue.

6. The computer-implemented method of claim 1, wherein the cytokine is one or more of TNF-α, TGF-β1, and/or HMGB1.

7. The computer-implemented method of claim 1, wherein the image output further comprises data relating to predicted hepatic inflammation state, inflammation-induced hepatic damage, hepatic viral load, virally-induced hepatic damage, hepatic tumor presence, hepatic tumor size, hepatic cancer presence, hepatic metastasis size, hepatic metastasis extent, hepatic fibrosis state, or any combination thereof.

8. The computer-implemented method of claim 1, wherein the data and rule are associated with an active agent, and wherein the image output comprises a representation of the effect of the active agent on hepatic inflammation, fibrosis, and/or cancer.

9. The computer-implemented method of claim 1, wherein, when the cytokine is TNF-α and the level of TNF-α at the first position is above a threshold cytokine value, the status of a hepatocyte at the second position is changed to dead cell.

10. The computer-implemented method of claim 1, wherein the data comprises data representing one or both of a hepatic lobule and a portal triad.

11. The computer-implemented method of claim 1, wherein the data comprises data representing one or more of hepatic septa, myofibroblasts, and collagen.

12. The computer-implemented method of claim 1, wherein the data comprises data representing an effect of an active agent on the at least one parameter.

13. The computer-implemented method of claim 1, wherein the data and rule are associated with simulating surgical removal of a simulated tumor with attendant tissue damage that stimulates further inflammation.

14. The computer-implemented method of claim 1, wherein the data and rule are associated with simulating a chemotherapeutic cytotoxic drug, such that simulated death of both tumor cells and hepatocytes occurs.

15. The computer-implemented method of claim 1, wherein the data and rule are associated with simulating an antiviral drug, such that both viral killing and inflammatory damage to the simulated liver tissue are simulated.

16. The computer-implemented method of claim 1, wherein the data and rule are associated with simulating an anti-inflammatory drug, such that reduction in inflammation and subsequent inflammatory damage to simulated liver tissue, immunosuppression, and virus growth-stimulating effects, are simulated.

17. The computer-implemented method of claim 1, wherein the data and rule are associated with simulating an anti-fibrotic drug, such that both reduction in fibrosis and subsequent inflammatory damage to simulated liver tissue, as well as suppression of tissue healing, are simulated.

18. A system comprising:

a display;

a processor; and memory having stored thereon programming instructions that when executed by the processor cause the processor to:

(i) receive data relating to at least one first parameter of a plurality of parameters associated with a hepatic condition in a patient, wherein the at least one first parameter is a level of at least one cytokine;

(ii) identify at least one first rule from a rules database, the at least one first rule comprising:

(a) determining a level of the cytokine at a first position associated with at least one hepatocyte;

(b) comparing the level of the cytokine at the position with a threshold cytokine value; and (c) changing a status of a second position based on the cytokine level;

(iii) generate a simulated progression of the hepatic condition by applying the at least one first rule to the data relating to the at least one first parameter, thereby generating a progression of the hepatic condition based on the at least one first rule;

(iv) generate, in a continuous space and based on the simulated progression, image output providing predicted hepatic tissue structure, the image output comprising representations of one or more of hepatocytes, stellate cells, and Kupffer cells;

(v) repeat steps (i)-(iv) to generate a stochastic range of the image output of the simulated progressions, the stochastic range of the image output comprising a plurality of images generated based on interactions among one or more of hepatocytes, stellate cells, and Kupffer cells based at least in part on the cytokine levels and the at least one first rule;

(vi) compare the stochastic range of image output of the simulated progressions with one or more liver biopsy images, the comparison comprising at least a comparison of one or more hepatocytes, stellate cells, and Kupffer cells; and (vii) determine, based at least on the comparing, a prognosis of the hepatic condition in the patient.

19. The system of claim 18, wherein the at least one processor is further programmed or configured to:

(viii) associate the image output to a matched liver biopsy image and store the associated data in a database.

20. The system of claim 19, wherein the at least one processor is programmed or configured to determine the prognosis based at least on: diagnostic information relating to the patient.

* * * * *